US008968777B2

(12) United States Patent
Heasley et al.

(10) Patent No.: US 8,968,777 B2
(45) Date of Patent: *Mar. 3, 2015

(54) TRANEXAMIC ACID FORMULATIONS WITH REDUCED ADVERSE EFFECTS

(75) Inventors: Ralph A. Heasley, Webster Grove, MO (US); Keith A. Moore, Loveland, OH (US); Jeffrey S. Greiwe, Ft. Thomas, KY (US); John W. Facemire, Douglasville, GA (US); Jason D. Modest, Minneapolis, MN (US)

(73) Assignee: Ferring B.V., Hoofddorp (NL)

( * ) Notice: Subject to any disclaimer, the term of this patent is extended or adjusted under 35 U.S.C. 154(b) by 2095 days.

This patent is subject to a terminal disclaimer.

(21) Appl. No.: 11/346,710

(22) Filed: Feb. 3, 2006

(65) Prior Publication Data

US 2006/0127476 A1 Jun. 15, 2006

Related U.S. Application Data

(63) Continuation-in-part of application No. 10/631,371, filed on Jul. 31, 2003, now abandoned.

(51) Int. Cl.
*A61K 9/22* (2006.01)
*A61K 9/20* (2006.01)
*A61K 31/195* (2006.01)

(52) U.S. Cl.
CPC .............. *A61K 9/2054* (2013.01); *A61K 9/2027* (2013.01); *A61K 31/195* (2013.01)
USPC ........................................................ 424/468

(58) Field of Classification Search
USPC ........................................................ 424/468
See application file for complete search history.

(56) References Cited

U.S. PATENT DOCUMENTS

| 3,870,790 | A | | 3/1975 | Lowey et al. |
| 4,171,377 | A | | 10/1979 | Green et al. ................... 514/561 |
| 4,258,030 | A | | 3/1981 | Sasaki et al. ..................... 424/94 |
| 4,389,393 | A | | 6/1983 | Schor et al. |
| 4,465,662 | A | | 8/1984 | Sato et al. ........................ 424/54 |
| 4,483,867 | A | | 11/1984 | Svahn et al. ................... 424/279 |
| 4,711,782 | A | | 12/1987 | Okada |
| 5,068,110 | A | | 11/1991 | Fawzi et al. |
| 5,229,135 | A | | 7/1993 | Philippon et al. ............. 424/494 |
| 5,242,337 | A | | 9/1993 | Greenwood ..................... 476/10 |
| 5,271,945 | A | | 12/1993 | Yoshioka |
| 5,506,264 | A | * | 4/1996 | Fujimura et al. ............... 514/494 |
| 5,575,987 | A | * | 11/1996 | Kamei et al. ................... 424/451 |
| 5,622,657 | A | | 4/1997 | Takada et al. ................ 264/4.32 |
| 5,650,174 | A | | 7/1997 | Muhammad et al. ......... 424/494 |
| 5,723,269 | A | | 3/1998 | Akagi |
| 5,738,874 | A | | 4/1998 | Conte et al. |
| 5,747,030 | A | | 5/1998 | Kohnert et al. ............ 424/94.64 |
| 5,807,583 | A | | 9/1998 | Kristensen et al. ........... 424/489 |
| 5,858,411 | A | | 1/1999 | Nakagami et al. ............ 424/489 |
| 5,874,463 | A | | 2/1999 | Ancira ........................... 514/460 |
| 5,877,175 | A | | 3/1999 | Sargent et al. |
| 5,897,910 | A | | 4/1999 | Rosenberg |
| 6,051,253 | A | | 4/2000 | Zettler |
| 6,056,977 | A | | 5/2000 | Bhagwat et al. |
| 6,066,339 | A | | 5/2000 | Stark et al. .................... 424/489 |
| 6,113,943 | A | | 9/2000 | Okada et al. .................. 424/457 |
| 6,120,802 | A | | 9/2000 | Breitenbach |
| 6,159,502 | A | | 12/2000 | Russell-Jones |
| 6,197,331 | B1 | * | 3/2001 | Lerner et al. .................. 424/448 |
| 6,274,171 | B1 | | 8/2001 | Sherman et al. |
| 6,300,369 | B1 | | 10/2001 | Ancira .......................... 514/460 |
| 6,328,979 | B1 | | 12/2001 | Yamashita et al. |
| 6,433,215 | B1 | | 8/2002 | Jung .............................. 560/220 |
| 6,548,084 | B2 | | 4/2003 | Leonard et al. ............... 424/482 |
| 6,551,616 | B1 | | 4/2003 | Notario et al. ................ 424/462 |
| 7,192,608 | B2 | | 3/2007 | Ochiai |
| 7,235,530 | B2 | | 6/2007 | Blair et al. ....................... 514/12 |
| 7,273,624 | B2 | | 9/2007 | Rosenberg et al. |
| 7,351,740 | B2 | | 4/2008 | Zerangue |
| 7,947,739 | B2 | | 5/2011 | Moore et al. |
| 8,022,106 | B2 | | 9/2011 | Moore et al. |
| 8,273,795 | B2 | | 9/2012 | Moore et al. |

(Continued)

FOREIGN PATENT DOCUMENTS

| CA | 2086565 | 7/1994 | |
| EP | 0998916 | 5/2000 | ............... A61K 9/00 |

(Continued)

OTHER PUBLICATIONS

Committee for Proprietary Medicinal Products (CPMP), Jul. 27, 2000, The Europen Agency for the Evaluation of Medicinal Products, Evaluation of Medicines for Human Use.*
Bonnar et al. (Treatment of menorrhagia during menstruation: randomized controlled trial of ethamsylate, mefenamic acid, and tranexamic) in the BMJ 1996; 313:579-582 (Sep. 7).*
Callender et al. ("treatment of Menorrhagia with Tranexamic Acid. A Double-blind Trial" in British Medical Journal, 1970, 4, 214-216).*
1996 PDR on Tranexamic acid (Cyklokapron), pp. 1950, 1951.*
Cooper et al. ("A randomized comparison of medical and hysteroscopic management in women consulting a gynecologist for treatment of heavy menstrual loss," in British journal of Obstetrics and Gynecology, vol. 104, pp. 1360-1366, 1997).*
Evonik—brochure—eudragit—product, Aug. 2012. V 2.3.*
U.S. Appl. No. 12/770,185, Patrick et al.
U.S. Appl. No. 12/714,181, Moore, et al.

(Continued)

*Primary Examiner* — Blessing M Fubara
(74) *Attorney, Agent, or Firm* — Fish & Richardson P.C.

(57) ABSTRACT

Tranexamic acid formulated in an oral dosage form with at least one agent that decreases tranexamic acid release in the stomach. Such formulations minimize nausea, vomiting, and other adverse gastric effects that may accompany tranexamic acid therapy, for example, to treat heavy menstrual bleeding. One embodiment is an extended release formulation with waxes, polymers, etc. that prevent a bolus release of tranexamic acid in the stomach. An alternative embodiment is a delayed release formulation with polymers that prevent release of tranexamic acid in the acid environment of the stomach and delay its release until the formulation reaches the less acid environment of the intestines. Such formulations enhance patient compliance with therapy because adverse effects of tranexamic acid therapy are reduced.

18 Claims, No Drawings

(56) References Cited

U.S. PATENT DOCUMENTS

| | | |
|---|---|---|
| 8,487,005 B2 | 7/2013 | Moore et al. |
| 8,791,160 B2 | 7/2014 | Moore et al. |
| 8,809,394 B2 | 8/2014 | Moore et al. |
| 2002/0132855 A1 | 9/2002 | Nelson et al. |
| 2003/0133985 A1 | 7/2003 | Louie-Helm et al. |
| 2003/0190353 A1 | 10/2003 | Oosterbaan et al. |
| 2004/0006021 A1 | 1/2004 | Rojkjaer .................. 514/12 |
| 2004/0052843 A1 | 3/2004 | Lerner et al. |
| 2004/0096499 A1 | 5/2004 | Vaya |
| 2004/0258753 A1 | 12/2004 | Demeesteer |
| 2005/0025825 A1 | 2/2005 | Moore et al. |
| 2005/0059742 A1 | 3/2005 | Jabbour et al. ............... 514/2 |
| 2005/0244495 A1 | 11/2005 | Moore et al. |
| 2005/0245614 A1 | 11/2005 | Moore et al. |
| 2005/0267014 A1 | 12/2005 | Rojkjaer et al. ........... 514/12 |
| 2006/0003006 A1 | 1/2006 | Remon |
| 2006/0018933 A1 | 1/2006 | Vaya et al. ............... 424/400 |
| 2006/0018934 A1 | 1/2006 | Vaya |
| 2006/0193914 A1 | 8/2006 | Ashworth |
| 2006/0287258 A1 | 12/2006 | Jabbour et al. ............ 514/15 |
| 2007/0020335 A1 | 1/2007 | Chen et al. ............... 424/468 |
| 2007/0027210 A1 | 2/2007 | Zerangue et al. ......... 514/533 |
| 2008/0193414 A1 | 8/2008 | Proudfoot |
| 2008/0280981 A1 | 11/2008 | Moore et al. |
| 2009/0017114 A1 | 1/2009 | Moore et al. |
| 2009/0048341 A1 | 2/2009 | Moore et al. |
| 2009/0209646 A1 | 8/2009 | Moore et al. |
| 2009/0214644 A1 | 8/2009 | Heasely et al. |
| 2009/0215898 A1 | 8/2009 | Moore et al. |
| 2010/0143468 A1 | 6/2010 | Moore et al. |
| 2010/0280117 A1 | 11/2010 | Patrick et al. |
| 2011/0230559 A1 | 9/2011 | Moore et al. |
| 2012/0122985 A1 | 5/2012 | Moore et al. |
| 2013/0012584 A1 | 1/2013 | Moore et al. |
| 2013/0018100 A1 | 1/2013 | Moore et al. |
| 2013/0096198 A1 | 4/2013 | Moore et al. |

FOREIGN PATENT DOCUMENTS

| | | | |
|---|---|---|---|
| EP | 0923934 | 8/2003 | |
| EP | 1 586 315 | 10/2005 | |
| GB | 2073019 | 10/1981 | ............... A61K 7/22 |
| JP | 57059847 | 4/1982 | |
| JP | 4-243825 | 8/1992 | |
| JP | 6219942 | 8/1994 | |
| JP | 7206660 | 8/1995 | |
| JP | 9077726 | 3/1997 | |
| JP | 9124878 | 5/1997 | |
| JP | 9255542 | 9/1997 | |
| JP | 10-017497 | 1/1998 | |
| JP | 2000-159674 | 6/2000 | |
| JP | 2001-163774 | 6/2001 | |
| JP | 2002-265358 | 9/2002 | |
| WO | 9415904 | 7/1994 | |
| WO | WO 96/19200 | 6/1996 | |
| WO | 2004028503 | 4/2004 | |
| WO | WO 2004/060364 | 7/2004 | |
| WO | WO 2005/011650 | 2/2005 | |
| WO | WO 2006/023000 | 3/2006 | |
| WO | WO 2006/023001 | 3/2006 | |
| WO | 2008111096 | 9/2008 | |
| WO | 2008148798 | 12/2008 | |

OTHER PUBLICATIONS

Alexander, D. A. et al, "Randomized trial comparing hysterectomy with endometrial ablation for dysfunctional uterine bleeding:•psychiatric and psychosocial aspects," BMJ, 1996, 312: 280-284.

Busija, L. et al, "Magnitude and meaningfulness of change in SF-36 scores in four types of orthopedic surgery", Health and Quality of Life Outcomes, 2008, 6:55.

Cella, D., Mayo Clinic Proc. vol. 77(4), Apr. 2002,384-392.

Cooper, Jay, MD et al, "A randomized, multicenter trial of safety and efficacy of the Nova Sure System in the treatment of Menorrhagia," J Am Assoc Gynecol Laparosc, 2002; 9 (4): 418-428.

Coulter, Angela et al, "Sharing decisions with patients: is the information good enough?" BMJ, 1999; 318: 318-322.

Chauhan, Cynthia, "Denouement: A Patient-Reported Observation," Value in Health, 2007; 10: suppl 2, 1098-3015/07/S146.

Crosignani, Pier Giorgio, MD et al, "Levonorgestrel-Releasing Intrauterine Device versus Hysteroscopic Endometrial Resection in the Treatment of Dysfunctional Uterine Bleeding," Obstet Gynecol, 1997, 90: No. 2.

Crosignani, Pier Giorgio, MD et al, "Endometrial resection versus vaginal hysterectomy for menorrhagia: Long-term clinical and quality-of-life Outcomes," Obstet Gynecol, 1997, 177: 95-101.

Coulter, A., et al, "Quality of Life and Patient Satisfaction Following Treatment for Menorrhagia," Family Practice, 1994; 11: No. 4.

"Committee for Proprietary Medicinal Products (CPMP) Opinion Following an Article 10 Referral. CYKLO-f," Jul. 2000.

Cooper, K., et al, "Comparison of microwave endometrial ablation and transcervical resection of the endometrium for treatment of heave menstrual loss: a randomized trial," The Lancet, 1999; 354.

Cooper, K. G. et al, "A randomized comparison of medical and hysterscopic management in women consulting a gynecologist for treatment of heavy menstrual loss," British Journal of Obstetrics and Gynaecology, 1997; 104: 1360.

Cooper, Kevin G. et al, "Two-year follow up of women randomized to medical management or transcervical resection of the endometrium for heavy menstrual loss: clinical and quality of life outcomes," British Journal of Obstetrics and Gynaecology, Mar. 1999; 106: 258-265.

Draft Guidance: Patient-reported Outcome Measures: Use in Medical Product Development to Support Labeling Claims, Feb. 2006.

Dueck, A., et al, "Meeting on the FDA Draft Guidance on Patient-Reported Outcomes," Value in Health, 2007; 10: suppl 2, S64-S65.

EuroQol Group, "Euro-Qol—a new facility for the measurement of health-related quality of life", health Policy, 16 (1990) 199-208.

Fraser, I. S., "Estimating Menstrual Blood Loss in women with Normal and Excessive Menstrual Fluid Volume," Obstet Gynecol, 2001; 98: 806-14.

Ferguson, R. J., et al., "Use of the Reliable Change index to evaluate Clinical significance in SF-36 Outcomes", Quality of Life Research, 11:509-6, 2002.

Frost, M.,et al, "What is Sufficient Evidence for the Reliability and Validity of Patient-Reported Outcome Measures?" Value in Health, 2007; 10: suppl 2, S94-S105.

Gath, D., et al, "Psychiatric disorder and gynaecological symptoms in middle aged women: a community survey," British Medical Journal, 1987; 294: 213.

Guyatt, G. H., MD et al, "Interpreting treatment effects in randomized trials," BMJ, 1998; 316.

Guyatt, G. H., MD et al, "Measuring disease-specific quality of life in clinical trials," CMAJ, 1986; 134: 889.

Guyatt, G.H., MD et al, "Postscript," Controlled Clinical Trials, 1991; 12: 266S-269S.

Garratt, A. M. et al, "The SF 36 health survey questionnaire: an outcome measure suitable for routine use within the NHS?" British Medical Journal, 1993; 306.

Garratt, A. M. et al, "SF 36 health survey questionnaire: II: Responsiveness to changes in health status in four common clinical conditions," Quality in Health Care, 1994; 3: 186-192.

Hurskainen, R., et al, "Quality of life and cost-effectiveness of levonorgestrel-releasing intrauterine system versus hysterectomy for treatment of menorrhagia: a randomized trial," The Lancet, 2001; 357.

Hurskainen, R., et al, "Combined Laboratory and diary method for objective Assessment of menstrual Blood loss"; Acta. Obstet. Gynecol. Scand. 1998, 77; 201-204.

Hays, R. D. et al, "The Rand 36-Item Health Survey 1.0," Health Economics, 1993; 2: 217-227.

Hays, j. et al., Effects of Estrogen plus Progestin on health Related Quality of Life: N. Engl. J. Med., 2003, 348: 1839-54.

Jaeschke, R., et al., "Ascertaining the Minimal Clinically Important Difference," Controlled Clinical Trials, 1989; 10: 407-415.

(56) References Cited

OTHER PUBLICATIONS

Jaeschke, R., et al, "Interpreting Changes in Quality-of-Life Score in N of 1 Randomized Trials," Controlled Clinical Trials, 1991; 12: 226S-233S.

Jenkinson, C., et al, "Making sense of ambiguity: evaluation of internal reliability and face validity of the SF 36 questionnaire in women presenting with menorrhagia," Quality in Health Care, 1996; 5: 9-12.

Jenkinson, C. et al, "Measuring change over time: a comparison of results from a global single item of health status and the multi-dimensional SF-36 health status survey questionnaire in patients presenting with menorrhagia," Quality of Life Survey, 1994; 3: 317-321.

Jones, G., et al, "Health-related quality of life measurement in women with common benign gynecologic conditions: A systematic review," AJOG Reviews, 2002; 187: 501-11.

Juniper, E., et al., "Determining a Minimal Improtant Change in a Disease-Specific Quality of Life Questionaire", J. Clin. Epidemlol. vol. 47, No. 1, 81-87, 1994.

Kadir, R.A. et al, "Quality of life during menstruation in patients with inherited bleeding disorders," Haemophilia, 1998; 4: 836-841.

Kennedy, A., et al, "Effects of Decision Aids for Menorrhagia on Treatment Choices, Health Outcomes and Costs," JAMA, 2002; 288: 2701-2708.

Kirshner, B., et al, "A Methodological Framework for Assessing Health Indices," J Chron Dis, 1985; 38: No. 1, 27-36.

Kjerulff, K. H., et al. "Patient satisfaction with results of hysterectomy", Am. J. Obstet. Gynecol., 2000; 183: 1440-7.

Kuppermann, M., et al, "Effect of Hysterectomy vs Medical Treatment on Health-Related Quality of Life and Sexual Functioning," JAMA, 2004; Mar. 2004; 291: No. 12.

Lethaby, A., et al. "Antifibrinolytics for heavy menstrual bleeding," The Cochrane Collaboration, 2002; issue 4.

Lamping, D. L. et al, "Development and validation of the menorrhagia outcomes questionnaires," British Journal of Obstetrics and Gynaecology, 1998; 105: 766-779.

Lohr, K., et al., evaluating Quality of Life and Health Status Instruments: Development of Scientific Review Criteria, Clin. Therapeutics, vol. 18, No. 5, 1996, 979.

Moos, K., MDQ Form C, published by Western Psychological Services, 1989.

Osoba, D., et al, "Evaluating Health-Related Quality of Life in Cancer Clinical Trials: The National Cancer Institute of Canada Clinical Trials Group Experience," Value in Health, 2007; 10: suppl 2, 1098-3015/07/S138.

Patrick, D. L., et al, "Patient-Reported Outcomes to Support Medical Product Labeling Claims: FDA Perspective," Value in Health, 2007; 10: suppl 2, 1098-3015/07/S125.

Patrick, D. L., et al, "Assessing the Clinical Significance of health related quality of life (HrQOL) improvements in anaemic cancer patients receiving epotin-alfa", European j. of Cancer, 39(2003) 335-345.

Patrick, D. L., et al. "Quality of Life of Women with Urinary Incontinence, Further development of the incontinence quality of Life Instrument (I-QOL)", Urology, 53: 71-76, 1999.

Philipp, C. S., et al, "Development of a screening tool for identifying women with menorrhagia for haemostatic evaluation," American Journal of Obstetrics and Gynecology, 2008; 1998: issue 2, 163.

Revicki, D. A, et al, "Interpreting and Reporting Results Based on Patient-Reported Outcomes," Value in Health, 2007; 10: suppl 2, 1098-3015/07/S138.

Reid, P. C., et al., "Assessment of Menstrual Blood Loss using a Pictorial Chart: a Validation Study " British L. Obstetrics and Gynaecology, Mar. 2000, vol. 107, pp. 320-322.

Richter, H. E., et al., "Medroxyprogesterone acetate treatment of abnormal uterine bleeding: Factors predicting satisfaction", Am. J. Obstet. Gynecol, Jul. 2003, pp. 37-42.

Rothman, M.L. et al., "Patient Reported Outcomes: Conceptual Issues", Value in Health, vol. 10 Supp. 2, 2007,pp. S66-S75.

Ruta, D. A. et al, "Patient centered assessment of quality of life for patients with four common conditions," Quality in Health Care, 1999; 8: 22-29.

Ruta, D. A. et al, SF 36 health survey questionnaire: I. Reliability in two patient based studies, Quality in Health Care, 1994; 3: 180-185.

Ruta, D. A. et al, Assessment of patients with Menorrhagia: how valid is a structured clinical history as a measure of health status, Quality of Life Research, 1995; 4: 33-40.

Sculpher, M.J., et al., "Randomized trial comparing hysterectomy and transcervical endometrial resection: effect on health related quality of life and costs two years after surgery", Br. J, of Obstet. Gynaecol., 1996, 103, 142-149.

Shaw, R. W. et al, "Perceptions of women on the impact of menorrhagia on their health using multi-attribute utility assessment," British Journal of Obstetrics and Gynaecology, Nov. 1998; 105: 1155-1159.

Shankar, M. et al, "Review of quality of life: Menorrhagia in women with or without inherited bleeding disorders," Haemophilia, 2008; 14: 15-20.

Sloan, J. A., et al. "Analysis and Interpretation of Results Based on Patient Reported Outcomes", ISPOR, Values in Health, 2007, 10, Supp2.,S106-S115.

Sloan, J. A., et al. "The Mayo Clinic manuscript Series Relative to the Discussion Dissemination, and Operationalization of the Food and Drug Administration Guidance on Patient Reported Outcomes",ISPOR, Values in Health, 2007, 10, Supp2.,S59-S63.

Smith, N. D., "Quality of Life Studies From the Perspective of an FDA Reviewing Statistician", Drug Inf. J. 1993, 27,617-623.

Snyder, C. F., et al., "Patient Reported Outcome Instrument Selection: Designing a Measuring Strategy" ISPOR, Values in Health, 2007, 10, Supp2.,S76-S85.

Spies, J.B., et al., "The UFS-QOL, a New Disease-Specific Symptom and Health-Related Quality of Life Questionnaire for Leiomyomata", Obstet Gynecol 2002, 99: 290-300.

Spies, J.B., et al., "The Fibroid Registry; Symptom and Quality of Life Status 1 Year After Therapy", Obstet Gynecol 2005,106: 1309-18.

Srinil, S., et al., "Treatment of Idiopathic Menorrhagia with Tranexamic Acid", J Med Assoc. Thai 2005; 88(Suppl. 2): S1-6.

Stanford School of Medicine, Div. Imm. & Rheu., "The Health Assessment Questionnaire", Jan. 19, 2001.

Turner, R. R., "Patient-Reported Outcomes: Instrument Development and Selection Issues," ISPOR, Value in Health, 2007; 10: supp. 2, S86-S93.

Wallenstein, G., et al., "Development and Validation of the Premenstrual Symptoms Impact Survey (PMSIS): A Disease-Specific Quality of Life Assessment Tool," Journal of Women's Health, 2008; 17: No. 3.

Ware, J. E., Jr. et al, "The MOS 36-Item Short-Form Health Survey (SF36)," Med. Care, 1992; 30: 473-483.

Warner, P.E. et al, "Menorrhagia I: Measured blood loss, clinical feathers, and outcome in women with heavy periods: A survey with follow-up data," Am. J. Obstetrics and Gynecology, 2004; 190: 1216-23.

Warner, P. E. et al, "Menorrhagia II: Is the 80mL blood loss criterion useful in management of complaint of menorrhagia?" Am. J. Obstetrics and Gynecology, 2004; 190: 1224-29.

Winkler, U. H., "The effect of tranexamic acid on the quality of life of women with heavy menstrual bleeding," European J.Obstetrics & Gynecology and Reproductive Biology, 2001; 99: 238-243.

Wilson, I.B., et al., "Linking Clinical Variables with Health Related Quality of Life: A Conceptual model of Patient Outcomes", JAMA 1995, 273(1), 59-65.

Wyrwich, K. W. et al., "Linking Clinical relevance and Statistical Significance in Evaluating Intra-Individual Changes in health Related quality of Life", Med. Care 1999 37(5), 469-478.

Wyrwich, K. W. et al., "Identifying meaningful intra-individual change standards for health related quality of life measures", J. Evaluation in Clinical Practice,2000, 6, 1, 39-49.

Wyrwich, K. W. et al., "Further Evidence Supporting an SEM-Based Criterion for Identifying Meaningful Intra-Individual Changes in health Related quality of Life", J Clin. Epidemiol. 2; 861-873.

(56) References Cited

OTHER PUBLICATIONS

Abbott, J. A., et al. "Quality of Life should Be Considered the Primary outcome for Measuring success of endometrial Ablation", J. Am. Assoc. Gynecol. Laparosc., 2003, 10(4); 491-495.
Ben-Tovim, D. I., et al., "The Influence of Age and Weight on Women's Body Attitudes as measured by the Body Attitudes Questionnaire (BAQ)" j. Psychosomatic Res., 1994,38(5) 477-481.
Carlson, K. J., et al. "The Maine Women's health Study: I. Outcomes of Hysterectomy", Obstet. Gynecol ,1994; 83: 556-65.
Cooper, K. et al, "Five-year follow-up of women randomized to medical management or transcervical resection of the endometrium for heavy menstrual loss: clinical and quality of life outcomes," *Br. J. Obstet. Gynaecol.*, 2001; 108: 1222-1228.
Coulter A., et. al. "Quality of Life and Patent Satisfaction Following Treatment for Menorrhagia"Family Practice, 1994:11(4); 394-401.
Deyo, R.A., et al., "Reproducibility and Responsiveness of Health Status Measures; Statistics and Strategies for Evaluation", Controlled Clinical Trials; 1991, 12, 142S-158S.
Liu, Z., et al., "A Systematic Review Evaluating health-Related Quality of Life, Work Impairment, and Health-Care Costs and Utilization in Abnormal Uterine Bleeding", ISPOR, Value in health, 2007; 10 (3), 183-194.
Greenberg Quinlan Rosner Research inc, "Survey of Women Who Experience Heavy Menstrual Bleeding" for Nation Women's Health Resource Center, Nov. 15, 2005.
Wiegel, M., et al., "The Female Sexual Function Index (FSFI): Cross Validation and Development of Clinical Cutoff Scores" , J Sex Martial Ther. 2005, 31; 1-20.
Dunn, C.J., et al., "Tranexamic Acid; A Review of its Use in Surgery and Other Indications", Drugs, Jun. 1999 57(6); 1005-1032.
Lamping D.L., et al., "Development and Validation of an Audit instrument: the Prostate Outcomes Questionnaire", Br. J. Urology, 1998, 82, 49-62.
Leidy, N. K. et al., "Recommendations for Evaluating the Validity of Quality of Life Claims for Labeling and Promotion", ISPOR, Value in health, 1999; 2(2), 113-127.
Lydick E., et al., "Interpretation of quality of life changes", Quality of life Research, 1993; 2, 221-226.
McHorney, C. A., et al, "The MOS 36-Item Short-Form Health Survey (SF36) II. Psychometric and Clinical Test of Validity in Measuring Physical and Mental Health Constructs", Med. Care, 1993; 31(3):247-263.
McHorney, C. A., et al, "The MOS 36-Item Short-Form Health Survey (SF36) III. Psychometric and Clinical Test of Data Quality, Scaling Assumptions, and Reliability Across Diverse Patient Groups", Med. Care, 1994; 32 (1):40-66.
Article: "Health-Related Quality of Life and Activity limitation—Eight States", 1995, MMWR, 1998, 47(7), 134-140.
Pawar, A. et al., "Perceptions about quality of life in a school-based population of adolescents with menorrhagia: implications for adolescents with bleeding disorders", Haemophilia, 2008, 14, 579-583.
Radloff, L. S., "The CES-D Scale: A Self Reported Depression Scale for Research in the General Population", App. Psychological. Measurement, 1977; 1(3), 385-401.
Shapley, M., et al. "Why women consult with increased vaginal bleeding: a case-control study", British Journal of General Practice, 2002,52, 108-113.
Shapley, M., et al. "An epidemiological survey of symptoms of menstrual loss in the community", British Journal of General Practice, 2004, 54; 359-363.
Silverman, E., "Your Drug Target Audience", The Scientist, Oct. 2007; 65-70.
Strik, J., et al., "Sensitivity and Specificity of Observer and Self-Report Questionnaires in major and minor Depression Following Myocardial Infarction" Psychosomatics, 2001: 42: 423-428.
Tapanainen, J. S., "Medical management of Menstrual Disorders" International Congress Series 1266(2004) 63-68.
Testa, M.A., et al., "Methods for Quality of Life Studies", Annu. Rev. Public Health. 1994, 15: 535-59.
Zee, B.C., "Growth Curve model Analysis for Quality of Life Data", Statist. Med., 17, 757-766(1998).
Cote I., et al., "Work Loss Associated With Increased Menstrual Loss in the United States", Obstet Gynecol, 2002; 100; 683-7.
Gorgen, H., et al., "Use of the Levonorgestrel-IUS in the treatment of menorrhagia: assessment of quality of life in Turkish users", Arch Gynecol Obstet, pub. Online Nov. 19, 2008.
Philipp, C. S.et al., "Age and the Prevalence of Bleeding Disorders in Women with Menorrhagia", Obstst Gynecol 2005; 105: 61-6.
Santer, M. et al., "what aspects of periods are most bothersome for women reporting heavy menstrual bleeding? Community survey and qualitative study", BMC Women's Health 2007, 7:8.
Protheroe, J., et al "The role of primary care in the diagnosis and management of menorrhagia: a qualitative study of women with menorrhagia", Primary Health Care Research and Development 2005: 6: 21-22.
Van Den Akker, O., et al. "Psycho physiological Responses in Women Reporting Severe Premenstrual Symptoms" Psychosomatic Medicine 51: 319-328 (1989).
Scientific Advisory Committee, "Assessing health status and quality of life instruments: Attributes and review criteria", Quality of Life Research 11: 193-205, 2002.
Flood, E.M., et al., "Psychometric evaluation of the Osteoporosis Patient Treatment Satisfaction Questionnaire (OPSAT-Q), a novel measure to assess satisfaction with bisphosphonate treatment in postmenopausal women" Health and Quality of Life Outcomes 2006, 4: 42.
Gumpel, J.M., et al., "Self-administered Clinical Questionnaire for outpatients", British Medical Journal, 174, 209-212.
New Zealand Working Party Guidelines, "An evidence-based guideline for the management of heavy menstrual bleeding", N Z Medical Journal , 1999, 112; 174-7.
FDA Guidance for Industry: Patient-Reported Outcome Measures: Use in Medical Product Development to Support Labeling Claims; Feb. 2006.
FDA Guidance for Industry: Patient-Reported Outcome Measures: Use in Medical Product Development to Support Labeling Claims; Dec. 2009.
Varner, R. et al., "Medicine or Surgery (MS); a randomized clinical trial comparing hysterectomy and medical treatment in premenopausal women with abnormal bleeding", Controlled Clinical Trials, 25 (2004) 104-118.
De Souza, S.S, et al., "Hemoglobin levels predict quality of life in women with heavy menstrual bleeding", Arch. Gynecol. Obstet., Aug. 20, 2009.
Park, Serena and Farquhar, CM, "A survey of practice preferences and attitudes of the New Zealand Guidelines for the management of heavy menstrual bleeding", Aust NZ J Obstet Gynaecol 2002; 42, 4:376, p. 377-80.
Quantification of Menstrual Blood Loss, Review, The Obstetrician & Gynaecologist, 2004; 6: p. 88-92.
Andersson .I, et al, "Role of Urokinase and Tissue Activator in Sustaining Bleeding and the Management Thereof with EACA and AMCA," *Annals N.Y. Acad. Sci.*, 146, p. 642-658.
Andersson L., et al, "Special Considerations with Regard to the Dosage of Tranexamic Acid in patients with Chronic Renal Diseases," *Urological Research* 6, 83-88 (1978).
Astedt, B., "Clinical Pharmacology of Tranexamic Acid", Scand. J. Gastroenterol, 1987, 22( Suppl 137), 22-25.
Bonnar J.et al., "Treatment of menorrhagia during menstruation: randomized controlled trial of ethamsylate, mefenamic acid, and tranexamic acid," *BMJ* 1996; 313: 579-82.
British national Formulary, ed?., Section 2.11 Antifibrinolytic drugs and Haemostatics, p. 123.
Callendar S., et al, "Treatment of Menorrhagia with Tranexamic Acid. A Double-blind Trial," *British Medical Journal*, 1970, 4, 214-216.
CPMP Opinion, *The European Agency for the Evaluation of Medicinal Products Evaluation of Medicines for Human Use*, Jul. 27, 2000—CPMP/902/00.
Dowd N., et al, "Pharmacokinetics of Tranexamic Acid during Cardiopulmonary Bypass," *Anesthesiology*, 2002; 97: 390-99.

(56) References Cited

OTHER PUBLICATIONS

Dockeray, C. et al, "The fibrinolytic enzyme system in normal menstruation and excessive uterine bleeding and the effect of tranexamic acid," *Eur. J. Obstet. Gynecol. Reprod. Biol.*, 24 (1987) 309-318.

Dubber, AHC., et al, "Some Properties of the antifibrinolytic active isomer of Amino-Methylclohexane Carboxylic Acid," *The Lancet*, 1964;2:1317-9.

Dubber, AHC. et al, "Amino Methyl Cyclohexane Carboxylic Acid (AMCHA), A New Synthetic Fibrinolytic Inhibitor," *British J Haemat*, 1965; 11: 237.

Eriksson O., et al, "Pharmacokinetics of Tranexamic Acid after Intravenous Administration to Normal Volunteers," *Europ. J. clin. Pharmacol.* 7, 375-380 (1974).

Gleeson, N. C. et al, "The effect of tranexamic acid on measured menstrual loss and endometrial fibinolytic enzymes in dysfunctional uterine bleeding," *Acta Obstet Gynecol Scand* 1994; 73: 274-277.

Hoylaerts, M., et al, "Studies on the Mechanism of the Antifibrinolytic Action of Tranexamic Acid," *Biochimica et Biophysica Acta*, 673 (1981) 75-85.

Kaller H., "Enterale Resorption, Verteilung und Elimination von 4-Ainomethylcyclohexancarbonsäure (AMCHA) und a-Aminocapronsäure (ACS) beim Menschen," *Naunyn-Schmiedeberts Arch. Pharmak. U. exp. Path.* 256, 160-168 (1967).

Lakhani, K. P. et al, "Uterine artery blood flow parameters in women with dysfunctional uterine bleeding and uterine fibroids: the effects of tranexamic acid," *Ultrasound Obstet Gynecol* (1998); 11: 283-285.

Lethaby, A. et al, "Antifibrinolytics for heavy menstrual bleeding (Review)," *The Cochrane Collaboration*, 2002; issue 4.

Lethaby, A. et al, "Antifibrinolytics for heavy menstrual bleeding (Review)," *The Cochrane Collaboration*, 2008; issue24.

Longstaff, C., "Studies on the mechanisms of action of aprotinin and tranexamic acid as plasmin inhibitors and antifibrinolytic agents," *Blood Coagulation and Fibrinolysis*, vol. 5, 1994, pp. 537-542.

Melander, B., et al, "Biochemistry and Toxicology of Amikapron®; The Antifibrinolytically Active Isomer of (AMCHA.) (A Comparative Study with Aminocaproic Acid)," *Acta Pharmacol. et Toxicol.* 1965, 22, 340-352.

Mohri, H., "High Dose of Tranexamic Acid for Treatment of Severe Menorrhagia in Patients with von Willebrand Disease," *Journal of Thrombosis and Thrombolysis*, 14 (3), 255-257, 2002.

Nilsson, I., "Clinical pharmacology of aminocaproic and tranexamic acids," *J Clin Pathod*, 33, Suppl (Roy Coll Path), 14, 41-47.

Nilsson, L and Rybo, G, "Treatment of Menorrhagia with an Antifibrinolytic Agent, Tranexamic Acid (AMCA)" *Acta obst. Et gynec. Scandinav.*, 46, 572, 1967.

Pilbrant A., et al, "Pharmacokinetcis and Bioavailability of Tranexamic Acid," *Eur J Clin Pharmacol*, (1961) 20: 65-72.

Preston J. T., et al, "Comparative study of tranexamic acid and norethisterone in the treatment of ovulatory menorrhagia," *British Journal of Obstetrics and Gynaecology*, May 1995, vol. 102, pp. 401-406.

Puigdellivol, E. et al, "Pharmacokinetics and absolute bioavailability of intramuscular tranexamic acid in man," *International Journal of Clinical Pharmacology, Therapy and Toxicology*, 1985; 23: No. 6, 298-301.

Rybo G., "Plasminogen Activators in the Endometrium, I. Methodological Apects" *Acta obst. et gynec. Scandinav*. 45, 411, 1966.

Svahn C M, et al, "Absorption of Tranexamic Acid as a Prodrug in Healthy Volunteers," *Arzneim-Forsch/Drug Res*. 38 (I), Nr. 5 (1988).

Svahn, Carl M., "Tranexamic Acid Derivatives with Enhanced Absorption," *J. Med Chem.*, 1986; 29: 448-453.

Tapanainen, Juha S., "Medical management of menstrual disorders," *International Congress Series*, 2004; 1266: 63-68.

Thorsen S., "Differences in the Binding to Fibrin of Native Plasminogen and Plasminogen Modified by Proteolytic Degradation Influence of w-Aminocarboxylic Acids," Biochimica et Biophysica Acta, 393 (1975) 55-65—Elsevier Scientific Publishing Company, Amsterdam.

Vermylen J., et al, "A double blind study of the effect of tranexamic acid in essential menorrhagia." *Throm Diath Haemorrh.*, Dec. 31, 1968; 20(3): 583-587.

Wellington K., et al, "Tranexamic Acid: A Review of its Use in the Management of Menorrhagia," *Drugs*, 2003:63(13): 1417-1433.

ACOG Practice Bulletin; "Management of anovulatory bleeding, 2000, No. 14", International J. Gynecology obstetrics 72(2001) 263-271.

Andersch, Björn et al, "An Objective Evaluation of Flurbiprofen and Tranexamic Acid in the Treatment of Idiopathic Menorrhagia," *Acta Obstet Gynecol Scand*, 1988; 67: 645-648.

Callender S., et al, "Treatment of Menorrhagia with Tranexamic Acid. A Double-blind Trial," *British Medical Journal*, 1970, 4, 214-216.

Dunn, C. J. et al, "Tranexamic Acid, A Review of its use in surgery and other indications," *Drugs*, 1999; 6: 1005-1032.

Edlund, M., et al, "Reduction of menstrual blood loss in women suffering from idiopathic menorrhagia with a novel antifibrinolytic drug (Kabi2161)," *British Journal of Obstetrics and Gynaecology*, 1995; 102: 913-917.

Hallberg, Leif et al, "Menstrual Blood Loss—A Population Study," *Goran, Acta obst. gynec. Scandinav*, 1966; 45: 320.

Higham, J. M. et al, "Risk-Benefit Assessment of Drugs Used for the Treatment of Menstrual Disorders," *Drug Safety*, 1991; 6(3): 183-191.

Kadir, R. A., et al, "Management of excessive menstrual bleeding in women with hemostatic disorders," *Fertility and Sterility*, 2005; 85(5), 1352-1359.

Kouides, PA et al, "Multisite management study of menorrhagia with abnormal laboratory haemostasis: a prospective crossover study of intranasal desmopressin and oral tranexamic acid," *Br J Haemotol*, 2009; 145(2): 212-220.

Lethaby A, Farquhar C, Cooke I. Antifibrinolytics for heavy menstrual bleeding. *Cochrane Database of Systematic Reviews* 2000, Issue4;. In The Cochrane Library, 2008 Issue 2.

Lockhart, I., Comments on MHRA Consultation Arm 39; Request to Reclassify CYKLO-F 500 Mg. Tablets (Tranexamic Acid) from Prescription only Medicine (POM) to Pharmacy available (P); royal College of Physicians of Edinburgh, , Feb. 27, 2007.

Mannucci, P.M., "Hemostatic Drugs", New England J. Medicine, vol. 339(4); 245-253.

Mehta, B.C. et al, "Epsilon-Amino-Caproic Acid in the Treatment of Menorrhagia," *Journal of Postgraduate Medicine*, 1977; 23(3): 121-123.

Milsom, I. et al, "A comparison of flurbiprofen, tranexamic acid, and a levonorgestrel-releasing intrauterine contraceptive device in the treatment of idiopathic menorrhagia," *Am J Obstet Gynecol*, 1991; 194: 879-883.

NICE Clinical Guideline 44, "Heavy Menstrual bleeding", Jan. 2007.
National Center for Women's and Children's Health; Heavy Menstrual Bleeding Full Guideline Draft, (Jul. 2006).

Nilsson, L , et al., "Treatment of Menorrhagia with an Antifibrinolytic Agent, Tranexamic Acid (AMCA)," *Acta obst. Et gynec. Scandinav.*, 46, 572, 1967.

Ogston, D, "Current Status of Antifibrinolytic Drugs," *Blood Reviews*, 1989; (3): 1-4.

Ong, Y.L. et al, "Menorrhagia in von Willebrand disease successfully treated with single daily dose tranexamic acid," *Haemophilia*, 1998, 4: 63-65.

Prentice, C.R.M., "Indications for Antifibrinolytic Therapy," *Thrombos. Diathes. Haemorrh.* (Stuttg.) 1975; 34: 634.

Popo, V., MHRA, Consultant Doc.: ARM 39, Request to Reclassify a product from POM to P; Cyklo-F, Feb. 7, 2007.

Ragab, M.I. et al, The Use of Tranexamic Acid (AMCA) in IUDs as an Anti-bleeding agent, *Int.J. Gynaecol Obstet*, 1976; 14:137-141.

Ranzcog, NHC Guidelines, Mar. 1999.

Rybo,"Tranexamic acid therapy—effective treatment in heavy menstrual bleeding." *Therapeutic Advances*, 1991; issue 4.

Shaw, R.W., "Assessment of medical treatments for Menorrhagia," *British Journal of Obstetrics and Gynaecology*, 1994; vol. 101, suppl. 11: 15-18.

Siegel, J.E. et al, "Menorrhagia from a haematologist's point of view. Part II: management," *Haemophilia*, 2002; 8: 339-347.

(56) References Cited

OTHER PUBLICATIONS

Srinil, Sukanya, MD, "Treatment of Idiopathic Menorrhagia the Tranexamic Acid," *J Med Assoc Thai*, 2005; 88: suppl 2.
van Eijkeren, M.A. et al, "Menorrhagia. Current Drug Treatment Concepts," *Drugs*, 1992; 43 (2): 201-209.
Vilos, GA, et al, "Guidelines for the management of abnormal uterine bleeding." J. Obstet. Gynaecol Can., 2001; 23; 704-709.
Weström, Lars, MD et al, "Effect of Tranexamic Acid (AMCA) in Menorrhagia with Intrauterine Contraceptive Devices," *J. of Reproductive Medicine*, 1970; 5: No. 4.
*Working Party for Guidelines for the Management of Heavy Menstrual Bleeding*. "An evidence-based guideline for the management of heavy menstrual bleeding," NZ Med J; 1999; 112: 174-7.
Ylikorkala, O., et al, "Comparison between antifibrinolytic and antiprostaglandin treatment in the reduction of increased menstrual blood loss in women with intrauterine contraceptive devices," *British Journal of Obstetrics and Gynaecology*, 1983; 90: 87-83.
Siegel, J.E. and Kouides, P.A., Menorrhagia from a haematologist's point of view. Part II: management, Haemophilia (2002), 8, p. 339-347.
Svahn, Carl M. et al, "Tranexamic Acid Derivatives with Enhanced Absorption", Journal of Medicinal Chemistry, 1986, vol. 29, No. 4, p. 448-453.
Marjoribanks, J. et al, "Surgery versus medical therapy for heavy menstrual bleeding (Review)", The Cochrane Library, 2009, Issue 2.
Apgar, Barbara S. et al, "Treatment of Menorrhagia", American Family Physician, Jun. 15, 2007, vol. 75, No. 12, p. 1813-1819.
Siddiquil, Shahnaz Hasan, "Spectrum of Dysfunctional Uterine Bleeding and its Conservative Management", JCPSP 2003, vol. 13 (7):375-377.
Tapanainen, Juha S., "Medical management of menstrual disorders", J.S. Tapanainen/International Congress Series 1266 (2004) 63-68.
Treatment and Management of Women with Bleeding Disorders, clinicaltrials.gov.
Kouides, Peter A., et al, "Multisite management study of Menorrhagia with abnormal laboratory haemostatis: a prospective crossover study of intranasal desmopressin and oral tranexamic acid", British Journal of Haematology, 145, p. 212-220.
Dr. Srinil, Sukanya and Dr. Jaisamrarn, Unnop, "Treatment of idiopathic menorrhagia with tranexamic acid", J Med Assoc Thai, vol. 88, suppl 2, 2005, p. S1-6.
Lee, J. et al., "Treatment of Menorrhagia with Tranexamic Acid," *J. Soc. Obstet. Gynaecol. Can.*, 2000;22(109):794-8.
Bekassy, Z. et al., "Treatment with the Fibrinolytic Inhibitor Tranexamic Acid—Risk for Thrombosis?" *Acta Obstet Gynecol Scand*, 1990; 69: 353-354.
Verstraete, M., "Clinical Application of Inhibitors of Fibrinolysis," *Drugs*, 29: 236-261 (1985).
Cyklokapron, Tranexamic acid tablets and injection, Pharmacia, 2001.
Cycklokapron Consumer Medicine Information.
Cyklokapron Tablets—Summary of Product Characteristics (SPC), http://emc.medicines.org.uk/medicine/16512/SPC/Cyklokapron+Tablets/.
Transamin Capsules (250mg), Tranexamic Acid Preparation, Product Description.
Transmin, Transamin cap approved prescribing info, MIMS Malaysia, http://www.mims.com/Page.aspx?menuid=mng&name=Transamin+cap&CTRY=MY&brief . . . , p. 1-6.
Transmin Tablets 500mg, Tranexamic Acid Preparation, Product Description, p. 1-2.
Package Leaflet: Information for the User, Cycklo-f-500 mg film-coated tablet, Tranexamic acid.
Tranexamic acid Product Description, p. T151-154.
Product Information, Cycklokapron, Tranexamic acid (CAS 1197-18-8), p. 1-8.
Cycklokapron, Tranexamic acid Tablets and Tranexamic acid injection, Product Description, p. 1-6.
Heavy Menstrual Bleeding, Clinical Guideline, Jan. 2007.
Hypromellose, Wikipedia definition, p. 1-3.
Cyckokapron, Tranexamic Acid, Data Sheet, http://www.medsafe.govt.nz/Profs/datasheet/c/Cyckloprontabinj.htm.
Cycklokapron, Tranexamic acid Tablets and Tranexamic acid injection, Antifibrinolytic agent, Pharmacia & Upjohn, p. 1-6.
Consultation Document: Arm 30, Request to Reclassify a Product from Pom to P, Safeguarding public health, Medicines and Healthcare products Regulatory Agency, Feb. 7, 2007.
Cycklokapron, Tranexamic acid tablets BP and Tranexamic acid injection BP, Product Monograph, Pfizer Canada Inc. Sep. 10, 2003.
Scientific Conclusions and Grounds for Amendment of the Summary of Product Characteristics Presented by the EMEA, Annex 1, p. 1-15.
Astedt, B., "Clinical Pharmacology of Tranexamic Acid", Scand J. Gastroenterol 1987, 22 (suppl 137), 22-25.
Dr. Giangrande, P.L.F. "Tranexamic Acid", http://www. Medicine.ox.ac.uk/ohc/tranexam.htm, p. 1.
Ansari, Tariq Mahmood, et al, "Spectrophotometric Determination of Tranexamic Acid in Pharmaceutical Bulk and Dosage Forms", Analytical Sciences, Sep. 2005, vol. 21, p. 1133-35.
Product Information: Cyklokapron Pharmacia; South Africa; 500mg tablets, 500mg IV, 1g effervescent tablets; package insert dated Dec. 1999.
Product Information: Cycklokapron Pharmacia; US, 500mg tablets, injection; package insert dated Oct. 2000.
Product Information: Cyklokapron KabiVitrumAB; US, 500mg tablets and injection; package insert dated Jan. 1987.
Product Information: Cyklokapron tablets (PfizerAu, approval 2001) with PI version pfpcyklt10308; PI Medsafe data sheet New Zealand 2008 (film coated tablet); and Pfizer data sheet (Spanish).
Product Information: Cyklonova 500mg film coated tablets; product Information date Oct. 5, 2007.
Product Information: Tranon 500mg film coated tablet, product information approved Apr. 16, 2008.
Product Information: Transamin Capsules, 250mg tablets, 500mg tablets, 50% powder, product information revision Jun. 2005.
Information Sheet: Transamin Otlo Pharmaceuticals, cap, tabs, injection.
Product Information: Transamin Capsules, dated Feb. 1998.
Information Sheet: Transamin Capsules, with Product Information: Transamin Tablets 500mg dated Feb. 1998.
Product Information: Cyklokapron Tablets 500 mg, product authorization Feb. 2005.
Product Information: Cyklokapron Tablets 500mg, film coat, product Jul. 31, 1968 with product information: cyklokapron 1000mg effervescent tablets, product authorization Dec. 7, 1995.
Product Information: Cycklo-f 500mg film coated tablet, authorization Jan. 31, 1997.
Product Information: Cyklokapron "Meda, Pfizer," injection, 500mg tablets, dated Oct. 24, 2006.
Product Information: Proklot film coated tablet, 500mg.
Product Information: Amchafibrin, 500mg.
Product Information: Tranexid, 250 mg capsules, 500mg membrane coated tablets.
Product Information: Tranfib, tablets and injection.
Product Information: Kalnex Capsules (250mg), tablets (500mg), injection, 1991.
Product Information: Hemostan 250, 500 mg capsules, injection.
Product Monograph: CykloKapron; Pfizer Canada Control No. 086534; Tranexamic acid tablets BP and Tranexamic acid injection BP date: Sep. 10, 2003, control No. 086534.
Martindale—revision Nov. 28, 2001, Monograph, Tranexamic acid (1726j).
Monograph: British Nat. Formulatry No. 43, 2002 sec. 2.11 Antifibrolytic drugs and haemostatics; Tranexamic acid pp. 123.
Information Sheet LExi-comp: Tranexamic Acid, Brand names.
Information Sheet Adam (internet) Tranexamic acid.
Monograph Health Canada; Cyklokapron; solution: for IV Use, date May 2005.
Product Information: Cyklokapron Injection, Ampoules 500mg per 5ml, Pharmacia Limited UK, authorization date Feb. 9, 1987.
Product Information: Cyklokapron tablets and Injection; 100mg/1ml water; Pharmacia & Upjohn revision Jun. 2008.
Product Information: Cyklokapron—tranexamic acid injection solution, 100mg/1ml. Pharmacia & Upjohn revision Jun. 2008.

(56) References Cited

OTHER PUBLICATIONS

Product Information: Cyklokapron—tranexamic acid injection solutions, 100mg/1ml. Pharmacia & Upjohn revision Jul. 2005, product registration, Jul. 31, 1968 (Dutch Language).
Product Information: Daiichi Pharmaceutical Co. Ltd., Transamin injection and Transamin S injection; 240mg/5ml, 250mg/2.5 ml and 1g/10ml.
CECMED Product Characteristics; ROTTAPHARMS S.L.; solution for Injection, IV, IV infusion, oral, 5mg/ml. vial.
Product Information: Dexa Medica, Traexid injection, injection 5% and injection 10%.
Product Information: Teva Pharmaceutical Industries Ltd., HEXAKAPRON; 500mg/5ml.
Quixil solutions for sealant, date of first authorization Sep. 1999.
Crotts, G et al., Development of an enteric coating formulation and process for tablets primarily composed of a highly water soluble organic acid: European. J. Pharmaceutics and Biopharmaceutics 51, (2001), 71-76.
Tsementzis, S.A., et al., "Fibrinolytic Activity After Subarachnoid Haemorrhage and the Effects of Tranexamic Acid," *Acta Neurochir* (Wien), vol. 103 (1990), pp. 116-121.
Patent Abstracts of Japan Publication No. JP 06219942, *Gelatin Capsule Preparation Mixed With Tranexamic Acid*, Published Aug. 9, 1994.
Patent Abstracts of Japan Publication No. JP 07206660, *External Preparation for Skin*, Published Aug. 8, 1995.
Patent Abstracts of Japan Publication No. JP 09124878, *Gel Composition*, Published May 13, 1997.
Patent Abstracts of Japan Publication No. JP 0925542, *Composition for Oral Cavity Application*, Published Sep. 30, 1997.
Patent Abstracts of Japan Publication No. JP 57059847, *4-Aminomethylcyclohexanecarboxylic Acid Derivative*, Published Apr. 10, 1982.
Walzman, M. and Bonnar, J. Effects of Tranexamic Acid on the Coagulation and Fibrinolytic Systems in Pregnancy Complicated by Placental Bleeding, *New Toxicology for Old Arch. Toxicol.*, Suppl. 5 (1982), pp. 214-220.
Erikkson, O. et al., "Pharmacokinetics of tranexamic acid after intravenous administration to normal volunteers," *Eur. J. Clin. Pharmacol*, 1974;7:375-380.
Berntorp E., "No increased Risk of Venous Thrombosis in Women Taking Tranexamic Acid," *Thromb Haemostat.*, 2001; 86: 714-5.
Sindet-Pedersen, "Distribution of tranexamic acid to plasma and saliva after oral administration and mouth rinsing: a pharmacokinetic study," *J. Clin. Pharmacol*. 1987; 27; 1005.
Physician's Desk Reference, 1996, on Tranexamic acid (Cyklokapron), pp. 1950-1951.
Kriplani, A. et al., "Role of tranexamic acid in management of dysfunctional uterine bleeding in comparison with medroxyprogesterone acetate," *Journal of Obstetrics and Gynaecology*, vol. 26, No. 7 (2006), pp. 673-678.
Demers, Christine et al., "Gynaecological and Obstetric Management of Women with Inherited Bleeding Disorders," *JOGC*, No. 163, Jul. 2005, pp. 707-718.
Product Information: Texamic Rx (Tranexamic acid tablets BP 500mg), marketed by Mefro Pharmaceuticals, Ltd., Manufactured by Terrace Pharmaceuticals, Ltd., p. 1.
EMEA, "Committee for Proprietary Medicinal Products Opinion Following an Article 10 Referral CYKLO-f (Tranexamic acid)", EMEA Jul. 27, 2000.
Product Information Cyklokapron® Pfizer Australia, most recent amendment Mar. 11, 2008, pp. 1-8.
Package Leaflet: Information for the user, Cyklonova 500mg film-coated tablet. Leaflet approved Dec. 12, 2005, pp. 1-3.
International Search Report from PCT/US2004/023528.
International Search Report from PCT/US2005/20558.
International Search Report from PCT/US2005/20563.
Pilbrant A, Schannong M, Vessman J., "Pharmacokinetics and bioavailability of tranexamic acid." *Eur J Clin Pharmacol* 1981;20:65-72.
Puigdellivol E, Carral M, Moreno J, et al., "Pharmacokinetics and absolute bioavailability of intramuscular tranexamic acid in man." *Int J Clin Pharmacol Therapy Toxicology* 1985;23:298-301.
Eriksson O, Kjellman H, Pilbrant A, et al., "Pharmacokinetics of tranexamic acid after intravenous administration to normal volunteers." *Eur J Clin Pharmacol* 1974;7:375-380.
Andersson I, Nilsson I, Colleen S, et al., "Role of urokinase and tissue activator in sustaining bleeding and the management thereof with EACA and AMCA." *Ann NY Acad Sci* 1968;146:642-658.
Dowd N, Karski J, Cheng D, et al. "Pharmacokinetics of Tranexamic Acid during Cardiopulmonary Bypass." *Anesthesiology* 2002;97:390-99.
Kaller H, "Enterale Resorption, Verteilung und Elimination von 4-Aminomethylcyclohexancarbonsäure (AMCHA) und a-Aminocapronsäure (ACS) beim Menshcen," *Naunyn-Schmiedebergs Arch. Pharmak.U. Exp Path*; 256: 160-169 (1967).
Andersson L, Eriksson O, Hedlund P, et al. "Special Considerations with Regard to the Dosage of Tranexamic Acid in Patients with Chronic Renal Diseases." *Urological Research* 6, 83-88 (1978).
Nilsson I, "Clinical pharmacology of aminocaproic and tranexamic acids." *J Clin Pathol*, 33, Suppl (Roy Coll Path), 14, 41-47.
Melander B, Gliniecki G, Granstrand B, et al. "Biochemistry and Toxicology of Amikapron®; The Antifibrinolytically Active Isomer of AMCHA. (A comparative Study with ∈-Aminocaproic Acid)" *Acta pharmacol. et toxicol*. 1965, 22, 340-352.
Longstaff C, "Studies on the mechanisms of action of aprotinin and tranexamic acid as plasmin inhibitors and antifibrinolytic agents." *Blood Coagulation and Fibrinolysis*, 5, 537-542. (1994).
Dockeray C, Sheppard B, Daly L, et al., "The fibrinolytic enzyme system in normal menstruation and excessive uterine bleeding and the effect of tranexamic acid." *Eur. J. Obstet. Gynecol. Reprod. Biol.*, 24 (1987) 309-318.
Mohri H., "High Dose of Tranexamic Acid for Treatment of Severe Menorrhagia in patients with von Willebrand Disease." *Journal of Thrombosis and Thrombolysis* 14(3), 255-257, (2002).
Preston J, Cameron I, Adams E, et al. "Comparative study of tranexamic acid and norethisterone in the treatment of ovulatory menorrhagia." *British Journal of Obstetrics and Gynaecology*, May 1995, vol. 102, pp. 401-406.
Bonnar J, Sheppard B. "Treatment of menorrhagia during menstruation: randomized controlled trial of ethamsylate, mefenamic acid, and tranexamic acid." *British Medical Journal* 1996;313:579-82.
Nilsson L, Rybo G. "Treatment of Menorrhagia with an Antifibrinolytic Agent, Tranexamic Acid (AMCA) A Double Blind Investigation." Nilsson, Lennart and Rybo, Göran, *Acta obst. Et gynec. scandinav*. 46, 572, (1967); 572-580.
Vermylen J, Verhaegen-Declercq M, Verstraete M, et al. "A Double Blind Study of the Effect of Tranexamic Acid in Essential Menorrhagia." From the Laboratory of Coagulation-Proteolysis, Department of Medicine, University of Leuven, Belgium. 583-587.
Callender S, Warner G, Cope E. "Treatment of Menorrhagia with Tranexamic Acid. A Double-blind Trial." *British Medical Journal*, 1970, 4, 214-216.
Andersch B, Milsom I, Rybo G. "An Objective Evaluation of Flurbiprofen and Tranexamic Acid in the treatment of Idiopathic Menorrhagia." *Acta Obstet Gynecol Scand* 67:645-648, 1988.
Milsom I, Andersson K, Andersch B, et al. "A comparison of flurbiprofen, tranexamic acid, and a levonorgestrel-releasing intrauterine contraceptive device in the treatment of idiopathic menorrhagia." *Am J Obstet Gynecol* 1991;164:879-83.
Gleeson N, Buggy F, Sheppard B, et al. "The effect of tranexamic acid on measured menstrual loss and endometrial fibrinolytic enzymes in dysfunctional uterine bleeding." *Acta Obstet Gynecol Scand* 1994; 73:274-277.
Lee J, Hahn P, Van Dijk J, et al. "Treatment of Menorrhagia with Tranexamic Acid." *J Soc Obstet Gynaecol Can* 2000;22(10):794-8.
Edlund M, Andersson K, Rybo G, et al., "Reduction of menstrual blood loss in women suffering from idiopathic menorrhagia with a novel antifibrinolytic drug (Kabi 2161)." *British Journal of Obstetrics and Gynaecology* 1995, vol. 102, pp. 913-917.
Winkler U. "The effect of tranexamic acid on the quality of life of women with heavy menstrual bleeding." *European Journal of Obstetrics & Gynecology and Reproductive Biology* 99 (2001) 238-243.

(56) References Cited

OTHER PUBLICATIONS

Rybo G., "Tranexamic acid therapy—effective treatment in heavy menstrual bleeding. Clinical update on safety." *Therapeutic Advances* ISSN 0964-0673 Issue 4. (1991).

Berntorp E. "No Increased Risk of Venous Thrombosis in Women Taking Tranexamic Acid." *Thromb Haemost* 2001; 86: 714-5.

Bekassy Z, Astedt B. "Treatment with the Fibrinolytic Inhibitor Tranexamic Acid—Risk for Thrombosis?" *Acta Obstet Gynecol Scand* 1990; 69: 353-354.

Mannucci P., "Hemostatic Drugs." *Drug Therapy*, vol. 339, No. 4, p. 245-253 (1998).

Wellington K, Wagstaff A., "Tranexamic Acid—A Review of its Use in the Management of Menorrhagia." *Adis Drug Evaluation, Drugs* 2003:63(13):1417-1433.

Dunn C, Goa K. "Tranexamic Acid—A Review of its Use in Surgery and Other Indications." *Adis Drug Evaluation, Drugs* Jun. 1999; 57 (6): 1005-1032.

"An evidence-based guideline for the management of heavy menstrual bleeding. Working Party for Guidelines for the Management of Heavy Menstrual Bleeding." *NZ Med J* 1999; 112: 174-7.

Lethaby A, Farquhar C, Cooke I. "Antifibrinolytics for heavy menstrual bleeding." *Cochrane Database of Syst Rev* 2002; (4).

Lakhani K, Marsh M, Purcell W. "Uterine artery blood flow parameters in women with dysfunctional uterine bleeding and uterine fibroids: the effects of tranexamic acid." *Ultrasound Obstet Gynecol* 1998;11:283-285.

Ong, Y., et al., "Menorrhagia in von Willebrand disease successfully treated with single daily dose tranexamic acid." *Haemophilia* (1998), 4, 63-65.

Patent Abstracts of Jpan Publiction No. JP 06219942. *Gelatin Capsule Preparation Mixed With Tranexamic Acid*. Published Aug. 9, 1994.

Patent Abstracts of Japan Publication No. JP 07206660, *External Preparation for Skin*. Published Aug. 8, 1995.

Patent Abstract of Japan Published No. JP 09124878. *Gel Composition*. Published May 13, 1997.

Cooper, K. G., et al., "A randomised comparison of medical and hysteroscopic management in women consulting a gynaecologist for treatment of heavy menstrual loss." *Br. J. Obstet.Gynaecol* vol. 104, pp. 1360-1366 (1997).

Cooper, K. G., et al., "Two-year follow up of women randomised to medical managament or transcervical resection of the endometrium for heavy menstrual loss: clinical and quality of life outcomes." *Br. J. Obstet.Gynaecol* vol. 106, pp. 258-265.

Mannucci, P.M., "Hemostatic Drugs" *New Eng. J. Medicine*,vol. 339, (4) pp. 245-253 (1998).

Tsementzis, S.A., et al."Fibrinolytic Activity After Subarachnoid Haemorrhage and the Effects of Tranexamic Acid" *Acta Neurochir* (Wien)vol. 103, pp. 116-121, (1990).

Ylikorkala, O., et al., "Comparison between antifibrinolytic and antiprostaglandin treatment in the reduction of increased menstrual blood loss in women with intrauterine contraceptive devices" *Br. J. Obstet.Gynaecol* vol. 90, pp. 78-83 (1983).

Walzman, M. and Bonnar, J., "Effects of Tranexamic Acid on the Coagulation and Fibrinolytic Systems in Pregnancy Complicated by Placental Bleeding", *New Toxicology for Old Arch. Toxicol*., Suppl. 5, 214-220 (1982).

Cyclokapron® Package Insert. Pharmacia & Upjohn. Revised Oct. 2000.

Cyklokapron® Package Insert. Pharmacia Canada, Inc. Misissauga, Ontario. (Nov. 2002).

Patent Abstracts of Japan Publication No. JP 09255542, Composition for Oral Cavity Application, Published Sep. 30, 1997.

Shaw, R.W., "Assessment of medical treatments for menorrhagia" *Br. J. Obstet. Gynaecol*, Suppl 11, vol. 101, pp. 15-18, (1994).

A brochure containing information relating to Tab. Trexamic and Tab. Trexamic-M.

Attorney B. Jefferson Boggs et al., Watson Laboratories, Inc., Florida's Initial Disclosure of Non-Infringement, Invalidity and Unenforceability Contentions to Ferring B.V., pp. 1 and 7-15, dated Jan. 5, 2012.

Attorney B. Neighbarger et al., First Amended Answer, Affirmative Defenses and Counter-claims to Complaint for Patent Infringement, Case No. 11-cv-00481-RCJ-VPC, D. Nev., 8 pp., dated Feb. 28, 2012.

Attorney B. Neighbarger et al., Second Amended Answer, Affirmative Defenses and Counter-claims to Complaint for Patent Infringement, Case No. 11-cv-00481-RCJ-VPC, D. Nev., 9 pp., dated Mar. 12, 2012.

Attorney Kevin W. McCabe, Notice Letter Regarding Paragraph IV Certification Against U.S. Patent No. 7947739 to Tranexamic Acid Formulations Pursuant to Section 505(j)(2)(B)(ii) of the Federal Food, Drug, and Cosmetic Act, dated May 27, 2011 (11 pp.).

Attorney Kevin W. McCabe, Notice Letter Regarding Paragraph IV Certification Against U.S. Patent No. 8022106 to Tranexamic Acid Formulations Pursuant to Section 505(j)(2)(B)(ii) of the Federal Food, Drug, and Cosmetic Act, dated Oct. 12, 2011 (10 pp.).

Attorney M. Rounds et al., First Amended Answer, Affirmative Defenses and Counter-claims to Complaint for Patent Infringement, Case No. 11-cv-004810RCJ-VPC, D. Nev., 16 pp., dated Feb. 28, 2012.

Attorney Michael D. Rounds et al., Watson's Points and Authorities in Opposition to Ferring's Motion to Dismiss Watons's Amended Second Counterclaims for Invalidity, Case No. 11-cv-00481-RCJ-VPC, D. Nev., 123 pp., dated Apr. 2, 2012.

Attorney Timothy Kratz, Notification of Paragraph IV Certification Regarding U.S. Patent No. 8,487,005 Pursuant to Section 505(j)(2)(B)(i)-(ii) of Federal Food, Drug, and Cosmetic Act, dated Aug. 29, 2013, 31 pp.

Aulton et al. Pharmaceutics The Science of Dosage and Design, Chapters 1 (pp. 1-11), 5 (pp. 62-80) and 18 (pp. 304-321) (1988).

Bradshaw et al., Answer to Complaint for Patent Infringement and Counterclaims, dated Feb. 15, 2013, 16 pg.

Bravo et al., "In-Vitro Studies of Diclofenac Sodium Controlled-release Biopolymeric Hydrophilic Matrices", *J. Pharm. Pharmaceut. Sci*., 2002, 5(3), 213-219.

Bushnell et al., "Menorrhagia Impact Questionnaire: assessing the influence of heavy menstrual bleeding on quality of life," *Current Med Res Opin*., 2010, 26(12), 2745-2755.

Cameron, Medical Management of Menorrhagia, *Curr. Obstet. Gynecol*., 1992, 2, 136-140.

Consumer Medicine Information leaflet, "Cyklokapron Tranexamic acid tablets and solution for injection", Pfizer Australia Pty Ltd 2010, 4 pp.

Dollery et al., Therapeutic Drugs, Second Edition, pp. T150-T154 (1999).

Dow Chemical Co., Formulating for Controlled Release with Methocel Cellulose Ethers (35 pp.) (1987).

Dow Chemical Co., Methocel as a Binding Agent for Tablet Production by Wet Granulation (14 pp.) (1985).

*Ferring B.V. v. Watson Labs., Inc*. Order by Robert C. Jones, U.S. District Judge, District of Neveda, dated Feb. 6, 2013, 19 pp.

Florence et al., "Novel Oral Drug Formulations, Their Potential in Modulating Adverse Effects" *Drug Safety*, 1994, 10(3) 233-266.

Friberg et al., "Bleeding disorders amount young women: A population-based prevalence study," Acta Obstertricia et Gynecologica Scandunavica, 2006, 85:200-206.

Investigative report dated Apr. 7, 2010 and prepared by Chief Investigator D.C. Sharma of ClueWise Services, Pvt. Ltd. (India) concerning information sought on Mefro Pharmaceuticals and Terrace Pharma (both of India), specifically in relation to a Trexamic Rx product (tranexamic acid) 3 pp.

Janet Vaughn, Director, Regulatory Affairs, Watson Laboratories Florida, Notification of Certification of Invalidity and/or Noninfringement for U.S. Patent No. 8,022,106 Pursuant to Section 505(j)(2)(B)(iv) of the Federal Food, Drug and Cosmetic Act, dated Oct. 12, 2011 (15 pp.).

Janet Vaughn, Director, Regulatory Affairs, Watson Laboratories Florida, Notification of Certification of Invalidity and/or

(56) References Cited

OTHER PUBLICATIONS

Noninfringement of U.S. Patent No. 7947739 Pursuant to Section 505(j)(2)(B)(iv) of the Federal Food, Drug, and Cosmetic Act, dated May 24, 2011 (16 pp.).
Janet Vaughn, Director, Regulatory Affairs, Watson Laboratories Florida, Notification of Invalidity and/or Noninfringement for U.S. Patent No. 8,273,795 Pursuant to §505(j)(2)(B)(iv) of the Federal Food, Drug, and Cosmetic Act, dated Nov. 5, 2012, 11 pp.
Janet Vaughn, Director, Regulatory Affairs, Watson Laboratories Florida, Notification of Invalidity and/or Noninfringement for U.S. Patent No. 8,487,005 Pursuant to § 505(j)(2)B(iv) of the Federal Food, Drug, and Cosmetic Act, dated Jul. 23, 2013, 11 pp.
Kouides et al., "Menorrhagia associated with laboratory abnormalities of hemostasis: epidemiological, diagnostic and therapeutic aspects," *J. Thromb. Haemost.*, 2007, 5 (Suppl. 1), 174-182.
Lamping, D.L. et al., "Development and validation of the menorrhagia outcomes questionnaires," *Brit. J. Obstet. Gynaecol.*, 1998, 105, 766-779.
Lee et al., "Controlled-Release Drug-Delivery Systems", Chapter 47 in Gennaro et al., Remington: The Science and Practice of Pharmacy, 20$^{th}$ Edition, Lippincott, Williams and Wilkins, pp. 903-929 (2000).
Lee et al., "Treatment of Menorrhagia with Tranexamic Acid," *Fertility and Sterility*, 1997, suppl. 1, 96.
Lethaby et al., Antifibrinolytics for Heavy Menstrual Bleeding, Cochrane Database of Systematic Reviews, Issue 4, 2002, (61 pp).
Levy et al., "Consider this option for heavy mentrual bleeding," *J. Fam. Pract.*, 2011, 60(7), 410-412.
Patel et al., "A comparative study of tranexamic acid and ethamsylate in menorrhagia," *Int. J. Basic Clin. Pharmacol.*, 2012, 1(2), 85-90.
Peterson et al., Treatment of Menorrhagia with Tranexamic Acid, *Acta Obstet. Gynecol. Scandinav.*, 1983, Supp. 116, pp. 70, 115.
Price list detailing the prices of numerous Mefro Pharmaceutical (P) LTD Products, including Tab, Trexamic and Tab trexamic-M, 8 pp.
Product catalog of Mefro Pharmaceuticals (P) LTD. that lists Tab Trexamic and Tab Trexamic-M as available products, 8 pp.
Product Information, Tranexamic Acid, downloaded from http://csi.micromedex.com/DKS/DATA/MT/MTMI/1726-j.HTM?Top=Yes (1 of 9) (2003).
Ross Maclean, VP Global Regulatory Affairs, Letter from Apotex Inc. to Ferring B.V., dated Nov. 5, 2012, 10 pg.
Rounds et al., Answer, Affirmative Defenses and Counter-Claims for Complaint for Patent Infringement, dated Feb. 28, 2013, 19 pp.
Shin-Yakuzaigaku Souron (New General Pharmaceutics), Nankodo, revised edition vol. 3, Apr. 10, 1987, pp. 287-291 (Note: An English translation of Table 10.2 is included), 6 pp.
Stavchansky and McGinity, "Bioavailability in Tablet Technology", Ch. 6, in Lieberman et al., Pharmaceutical Dosage Form, 2nd Ed., vol. 2, Marcel Dekker, pp. 349-569 (1990).
Stirrat, Gordon M., "Choice of treatment for menorrhagia," *Lancet*, 1999, 353, 2175-2176.
Wilson et al., "Physiological Pharmaceutics Biological Barriers to Drug Absorption", Horwod Ellis, Chichester, Chapter 4, pp. 47-70 (1989).
Advisory Action dated Oct. 23, 2007 for U.S. Appl. No. 10/631,371, 3 pp.
Advisory Action dated Dec. 12, 2011 for U.S. Appl. No. 12/228,489, 5 pp.
Applicant's Accelerated Examination Support Document filed Feb. 26, 2010, U.S. Appl. No. 12/714,181, 6 pp.
Applicant's Pre-examination Search Statement filed Feb. 26, 2010, U.S. Appl. No. 12/714,181, 6 pp.
Applicant's Response to Final Office Action dated Jun. 14, 2007, filed Oct. 4, 2007, U.S. Appl. No. 10/631,371.
Applicant's Response to non-final Office Action dated Dec. 15, 2006, filed Mar. 13, 2007, U.S. Appl. No. 10/631,371, 9 pp.
Applicant's Amendment in Reply to Action filed May 9, 2011, U.S. Appl. No. 12/228,489, 18 pp.
Applicant's Reply to Final Office Action filed Nov. 9, 2011, U.S. Appl. No. 12/228,489, 13 pp.
Decision by USPTO dated Mar. 31, 2010 for Petition to Make Special, U.S. Appl. No. 12/714,181, 4 pp.
Final Rejection dated Oct. 12, 2010 for Japanese Appl. No. 2006-521917 (with English translation), 6 pp.
Final Rejection mailed Jan. 7, 2014, for Japanese Appl. No. 2011-062281, 3 pp. (with English translation).
Notice of Allowance dated Apr. 8, 2011, U.S. Appl. No. 12/714,181, 9 pp.
Notice of Allowance dated May 10, 2013 for U.S. Appl. No. 13/620,148, 32 pp.
Notice of Allowance dated Nov. 4, 2013, for U.S. Appl. No. 13/016,800, 30 pp.
Notice of Allowance dated Aug. 5, 2011 for U.S. Appl. No. 12/433,510, 7 pp.
Notice of Panel Decision from Pre-Appeal Brief Review dated Feb. 7, 2013 for U.S. Appl. No. 12/433,247, 2 pp.
Notice of Rejection dated Aug. 17, 2010 for Japanese Appl. No. 2007-523556 (with English translation), 11 pp.
Notice of Rejection dated Aug. 2, 2011, Japanese Appl. No. 2006-521917, 3 pp.
Notice of Rejection dated Aug. 2, 2011, Japanese Appl. No. 2011-028472, 7 pp.
Notice of Rejection dated Dec. 20, 2011, Japanese Appl. No. 2007-523555, 3 pp.
Notice of Rejection dated Jan. 29, 2013 for Japanese Appl. No. 2011-062281, 5 pp.
Notice of Rejection dated Oct. 25, 2011, Japanese Appl. No. 2007-523556, 2 pp.
Notice of Rejection dated Sep. 29, 2009 for Japanese Appl. No. 2006-521917 (with English translation), 25 pp.
Notice of Rejection dated Sep. 3, 2010 for Japanese Appl. No. 2007-523555 (with English translation), 11 pp.
Office Action (Examiner Interview Summary Record) dated Oct. 28, 2008 for U.S. Appl. No. 10/631,371, 2 pp.
Office Action (Final Rejection) dated Jun. 14, 2007 for U.S. Appl. No. 10/631,371, 9 pp.
Office Action (Final Rejection) dated Sep. 9, 2010 for U.S. Appl. No. 12/220,241, 8 pp.
Office Action (final) dated Jun. 28, 2012 for U.S. Appl. No. 12/433,247, 21 pp.
Office Action (final) dated Aug. 25, 2010, U.S. Appl. No. 12/714,181, 11 pp.
Office Action (final) dated Aug. 9, 2011 for U.S. Appl. No. 12/228,489, 38 pp.
Office Action (final) dated May 11, 2011 for U.S. Appl. No. 12/433,510, 4 pp.
Office Action (non-final) dated Mar. 18, 2013 for U.S. Appl. No. 13/016,800, 9 pp.
Office Action (non-final) dated Oct. 25, 2011 for U.S. Appl. No. 12/433,247, 18 pp.
Office Action (non-final) dated Dec. 15, 2006 for U.S. Appl. No. 10/631,371, 6 pp.
Office Action (non-final) dated Mar. 13, 2008 for U.S. Appl. No. 10/631,371, 7 pp.
Office Action (non-final) dated Feb. 5, 2010 for U.S. Appl. No. 12/220,241, 7 pp.
Office Action (non-final) dated Jan. 23, 2008 for U.S. Appl. No. 11/072,162, 6 pp.
Office Action (non-final) dated Jul. 30, 2010 for U.S. Appl. No. 12/433,408, 7 pp.
Office Action (non-final) dated May 10, 2010 for U.S. Appl. No. 12/433,510, 9 pp.
Office Action (non-final) dated Oct. 28, 2010 for U.S. Appl. No. 12/433,510, 11pp.
Office Action (non-final) dated Apr. 27, 2010 for U.S. Appl. No. 12/714,181, 8 pp.
Office Action (non-final) dated Jul. 1, 2010, U.S. Appl. No. 12/714,181, 11 pp.
Office Action (non-final) dated Oct. 18, 2013, for U.S. Appl. No. 12/770,185, 15 pp.
Office Action (non-final) dated Feb. 28, 2013, U.S. Appl. No. 12/770,185, 5 pp.

(56) References Cited

OTHER PUBLICATIONS

Office Action (non-final) dated Nov. 8, 2010 for U.S. Appl. No. 12/228,489, 16 pp.
Office Action (non-final) dated Aug. 6, 2013 for U.S. Appl. No. 13/230,902, 31 pp.
Office Action (non-final) dated Dec. 3, 2010, U.S. Appl. No. 12/714,181, 17 pp.
Office Action dated Jun. 29, 2011 for U.S. Appl. No. 12/283,694, 27 pp.
Office Action dated Mar. 1, 2012 for U.S. Appl. No. 12/283,694, 18 pp.
Office Action (Final) dated Jun. 18, 2014, for U.S. Appl. No. 12/770,185, 10 pages.
Office Action (Non-Final) dated Jun. 17, 2014, for U.S. Appl. No. 13/230,902, 13 pages.
U.S. Court of Appeals for the Federal Circuit, *Ferring B.V.* v. *Watson Laboratories, Inc.*, Appeal No. 2014-1377, Aug. 22, 2014, 17 pp.
U.S. Court of Appeals for the Federal Circuit, *Ferring B.V.* v. *Watson Laboratories, Inc.*, Appeal No. 2014-1416, Aug. 22, 2014, 19 pp.

\* cited by examiner

TRANEXAMIC ACID FORMULATIONS WITH REDUCED ADVERSE EFFECTS

This application is a continuation-in-part application of U.S. patent application Ser. No. 10/631,371, filed Jul. 31, 2003, the disclosure of which is hereby incorporated by reference in its entirety.

FIELD OF THE INVENTION

The invention is directed to therapeutic oral tranexamic acid formulations that minimize or eliminate undesirable side effects.

BACKGROUND

Tranexamic acid (trans-4-(aminomethyl) cyclohexanecarboxylic acid, Cyklokapron® (Pfizer) is an antifibrinolytic agent. That is, it helps to prevent lysis or dissolution of a fibrin clot which forms in the normal physiologic process of hemostasis. Its mechanism of action is as a competitive inhibitor of plasminogen activation, and as a noncompetitive inhibitor of plasmin; both plasminogen and plasmin are activators of fibrinolyis and active clot-lysing agents. Tranexamic acid thus helps to stabilize fibrin clots, which in turn maintains coagulation and helps to control bleeding.

Tranexamic acid is used to control excess bleeding, for example, excess bleeding that occurs during dental procedures in hemophiliacs and for heavy bleeding during menstruation (menorrhagia). Women suffering from menorrhagia are typically treated orally with 500 mg tranexamic acid tablets administered three or four times daily with a total daily dose ranging from 3 grams/day (two tablets every eight hours) to 6 grams/day (three tablets every six hours). However, this treatment may cause adverse gastrointestinal reactions, including nausea, vomiting, diarrhea, and cramping, etc. These gastrointestinal side effects are due to the quantity of tranexamic acid introduced into the stomach with each dose, as well as the large quantity of excipients used in tablet formulation that are introduced into the stomach. Such side effects, in addition to the cramping, bloating, pain, and other symptoms that may accompany menses, are undesirable, and a formulation of tranexamic acid is needed which will reduce or eliminate these side effects.

SUMMARY OF THE INVENTION

Formulations of tranexamic acid which minimize or eliminate the undesirable gastrointestinal side effects in patients on oral tranexamic acid therapy, e.g. women treated for menorrhagia (heavy menstrual bleeding), by modifying the release characteristics of tranexamic acid are disclosed. One embodiment is an extended release formulation, also termed a controlled release formulation, formulated so that the release of tranexamic acid from the dosage form occurs in an extended or controlled fashion to prevent a bolus of tranexamic acid being introduced into the stomach and available for dissolution in the gastric contents. An alternative embodiment is a delayed release formulation. Delayed release dosage forms are formulated to minimize or prevent the dissolution of the drug in the stomach. The release of tranexamic acid is delayed until the dosage form exits the stomach and reaches the small intestine. Both extended release dosage forms and delayed release dosage forms are termed modified release dosage forms. Such modified release formulations reduce the concentration of tranexamic acid dissolved in the stomach contents. The beneficial effect of this reduced tranexamic acid concentration is to lower the amount of tranexamic acid in the gastric contents so that there are fewer gastric adverse effects with tranexamic acid therapy. This reduction in gastric adverse effects results in improved patient compliance with therapy, because patients will not intentionally miss taking a dose to avoid these adverse side effects. Physicians will also be more likely to initiate and maintain tranexamic acid treatment for their patients because of the reduced patient complaints.

It is an object of the invention to provide an oral dosage form comprising tranexamic acid which is suitable for administration on a two or three times a day basis to humans.

It is an object of the invention to provide a modified release oral dosage form comprising tranexamic acid and a modified release material which provides for the modified release of the tranexamic acid and is suitable for administration on a two or three times a day basis.

It is an object of the invention to provide a delayed release oral dosage form comprising tranexamic acid and a delayed release material which provides for the delayed release of the tranexamic acid and is suitable for administration on a two or three times a day basis.

It is a further object of certain embodiments of the present invention to provide a modified release oral dosage form comprising tranexamic acid and a modified release material which minimizes or eliminates the undesirable gastrointestinal side effects in patients on oral tranexamic acid therapy while maintaining or improving the therapeutic effect of tranexamic acid.

It is a further object of certain embodiments of the present invention to provide a delayed release oral dosage form comprising tranexamic acid and a delayed release material which minimizes or eliminates the undesirable gastrointestinal side effects in patients on oral tranexamic acid therapy while maintaining or improving the therapeutic effect of tranexamic acid.

It is a further object of certain embodiments of the present invention to provide a method of treating a patient suffering from heavy menstrual bleeding (menorrhagia) by orally administering to the patient one or more dosage forms comprising tranexamic acid and a modified release material which provide(s) for therapeutically effective levels of tranexamic acid suitable for two or three times a day administration.

It is a further object of certain embodiments of the present invention to provide a method of treating a patient suffering from heavy menstrual bleeding (menorrhagia) by orally administering to the patient one or more dosage forms comprising tranexamic acid and a delayed release material which provide(s) for therapeutically effective levels of tranexamic acid suitable for two or three times a day administration.

The above advantages and objects and others can be achieved by virtue of the present invention which is directed in part to a modified release oral dosage form comprising tranexamic acid and a modified release material which provides for the modified release of the tranexamic acid from the dosage form such that the dosage form is suitable for administration on a two or three times a day basis.

In certain embodiments, the present invention is further directed to a delayed release oral dosage form comprising tranexamic acid and a delayed release material which provides for the delayed release of the tranexamic acid from the dosage form such that the dosage form is suitable for administration on a two or three times a day basis.

In certain embodiments, the present invention is directed to a delayed release oral dosage form comprising tranexamic acid or a pharmaceutically acceptable salt thereof and a delayed release material which provides for the delayed release of the tranexamic acid such that the dosage form is suitable for administration on a two or three times a day basis; said dosage form providing an in-vitro dissolution release rate of the tranexamic acid or pharmaceutically acceptable salt thereof when measured by the USP 27 Dissolution Apparatus Type II Paddle Method @ 50 RPM and 37±0.5° C. of less than about 10% by weight tranexamic acid or pharmaceutically acceptable salt thereof released by about 120 minutes in acid medium (1000 ml of 0.1N hydrochloric acid), and at least about 75% by weight of said tranexamic acid or pharmaceutically acceptable salt thereof released by about 45 minutes after subsequent immersion in buffer medium (1000 ml of pH 6.8 phosphate buffer), preferably less than about 5% by weight tranexamic acid or pharmaceutically acceptable salt thereof released by about 120 minutes in the acid medium and at least about 90% by weight tranexamic acid or pharmaceutically acceptable salt thereof released by about 45 minutes after subsequent immersion in the buffer medium.

In certain embodiments, the present invention is further directed to a modified release oral dosage form comprising from about 585 to about 715 mg of tranexamic acid or pharmaceutically acceptable salt thereof, preferably from about 617 to about 683 mg of tranexamic acid or pharmaceutically acceptable salt thereof, more preferably about 650 mg of tranexamic acid or pharmaceutically acceptable salt thereof, and a modified release material which provides for the modified release of the tranexamic acid or pharmaceutically acceptable salt thereof from the dosage form such that the dosage form is suitable for administration on a two or three times a day basis.

In certain embodiments, the present invention is further directed to a delayed release oral dosage form comprising from about 585 to about 715 mg of tranexamic acid or pharmaceutically acceptable salt thereof, preferably from about 617 to about 683 mg of tranexamic acid or pharmaceutically acceptable salt thereof, more preferably about 650 mg of tranexamic acid or pharmaceutically acceptable salt thereof, and a delayed release material which provides for the delayed release of the tranexamic acid or pharmaceutically acceptable salt thereof from the dosage form such that the dosage form is suitable for administration on a two or three times a day basis.

In certain embodiments, the present invention is directed to a modified release oral dosage form comprising tranexamic acid or pharmaceutically acceptable salt thereof and a modified release material which provides for the modified release of the tranexamic acid or pharmaceutically acceptable salt thereof from the dosage form such that the dosage form is suitable for administration on a two or three times a day basis, the dosage form providing a reduction of at least one side effect selected from the group consisting of headache, nausea, vomiting, diarrhea, constipation, cramping, bloating, and combinations thereof, as compared to an equivalent amount of tranexamic acid or pharmaceutically acceptable salt thereof in an immediate release oral dosage form when administered across a patient population.

In certain embodiments, the present invention is directed to a delayed release oral dosage form comprising tranexamic acid or pharmaceutically acceptable salt thereof and a delayed release material which provides for the delayed release of the tranexamic acid or pharmaceutically acceptable salt thereof from the dosage form such that the dosage form is suitable for administration on a two or three times a day basis, the dosage form providing a reduction of at least one side effect selected from the group consisting of headache, nausea, and combination thereof, as compared to an equivalent amount of tranexamic acid or pharmaceutically acceptable salt thereof in an immediate release oral dosage form when administered across a patient population.

In certain embodiments, the invention is further directed to a method of treating a patient with a therapeutically effective amount of tranexamic acid or pharmaceutically acceptable salt thereof comprising administering to the patient two dosage forms of the present invention, each dosage form comprising from about 585 mg to about 715 mg of tranexamic acid or pharmaceutically acceptable salt thereof, preferably from about 617 to about 683 mg of tranexamic acid or pharmaceutically acceptable salt thereof, more preferably about 650 mg tranexamic acid or pharmaceutically acceptable salt thereof, and a modified release material such that the dosage form is suitable for oral administration on a three times a day basis.

In certain embodiments, the invention is further directed to a method of treating a patient with a therapeutically effective amount of tranexamic acid or pharmaceutically acceptable salt thereof comprising administering to the patient two dosage forms of the present invention, each dosage form comprising from about 585 mg to about 715 mg of tranexamic acid or pharmaceutically acceptable salt thereof, preferably from about 617 to about 683 mg of tranexamic acid or pharmaceutically acceptable salt thereof, more preferably about 650 mg tranexamic acid or pharmaceutically acceptable salt thereof, and a delayed release material such that the dosage form is suitable for oral administration on a three times a day basis.

In certain embodiments, the invention is further directed to a method of treating a patient with a therapeutically effective amount of tranexamic acid or pharmaceutically acceptable salt thereof comprising administering to the patient three dosage forms of the present invention, each dosage form comprising from about 585 mg to about 715 mg tranexamic acid or pharmaceutically acceptable salt thereof, preferably from about 617 to about 683 mg of tranexamic acid or pharmaceutically acceptable salt thereof, more preferably about 650 mg tranexamic acid or pharmaceutically acceptable salt thereof, and a modified release material such that the dosage form is suitable for oral administration on a twice a day basis.

In certain embodiments, the invention is further directed to a method of treating a patient with a therapeutically effective amount of tranexamic acid or pharmaceutically acceptable salt thereof comprising administering to the patient three dosage forms of the present invention, each dosage form comprising from about 585 mg to about 715 mg tranexamic acid or pharmaceutically acceptable salt thereof, preferably from about 617 to about 683 mg of tranexamic acid or pharmaceutically acceptable salt thereof, more preferably about 650 mg of tranexamic acid or pharmaceutically acceptable salt thereof, and a delayed release material such that the dosage form is suitable for oral administration on a twice a day basis.

In certain embodiments, the invention is directed to a dose of tranexamic acid or pharmaceutically acceptable salt thereof comprising two unit dosage forms of a modified release formulation, each unit dosage form of said modified release formulation comprising from about 585 mg to about 715 mg of tranexamic acid or pharmaceutically acceptable salt thereof, preferably from about 617 to about 683 mg of tranexamic acid or pharmaceutically acceptable salt thereof, more preferably about 650 mg of tranexamic acid or pharmaceutically acceptable salt thereof, and a modified release material which provides for the release of the tranexamic acid or pharmaceutically acceptable salt thereof from the dosage form such that the dose provides a therapeutic effect when administered three times a day.

In certain embodiments, the invention is directed to a dose of tranexamic acid or pharmaceutically acceptable salt thereof comprising two unit dosage forms of a delayed release formulation, each unit dosage form of said delayed release formulation comprising from about 585 mg to about 715 mg tranexamic acid or pharmaceutically acceptable salt thereof, preferably from about 617 to about 683 mg of tranexamic acid or pharmaceutically acceptable salt thereof, more preferably about 650 mg of tranexamic acid or pharmaceutically acceptable salt thereof, and a delayed release material which provides for the release of the tranexamic acid or pharmaceutically acceptable salt thereof from the dosage form such that the dose provides a therapeutic effect when administered three times a day.

In certain embodiments, the invention is directed to a dose of tranexamic acid comprising three unit dosage forms of a modified release formulation, each unit dosage form of said modified release formulation comprising from about 585 mg to about 715 mg tranexamic acid or pharmaceutically acceptable salt thereof, preferably from about 617 to about 683 mg of tranexamic acid or pharmaceutically acceptable salt thereof, more preferably about 650 mg of tranexamic acid or pharmaceutically acceptable salt thereof, and a modified release material which provides for the release of the tranexamic acid or pharmaceutically acceptable salt thereof from the dosage form such that the dose provides a therapeutic effect when administered twice a day.

In certain embodiments, the invention is directed to a dose of tranexamic acid comprising three unit dosage forms of a delayed release formulation, each unit dosage form of said modified release formulation comprising from about 585 mg to about 715 mg tranexamic acid or pharmaceutically acceptable salt thereof, preferably from about 617 to about 683 mg of tranexamic acid or pharmaceutically acceptable salt thereof, more preferably about 650 mg of tranexamic acid or pharmaceutically acceptable salt thereof, and a delayed release material which provides for the release of the tranexamic acid or pharmaceutically acceptable salt thereof from the dosage form such that the dose provides a therapeutic effect when administered twice a day.

In certain embodiments, the invention is further directed to a modified release oral dosage form comprising tranexamic acid or pharmaceutically acceptable salt thereof and a delayed release material which provides for the delayed release of the tranexamic acid or pharmaceutically acceptable salt thereof from the dosage form such that the dosage form is suitable for administration on a two or three times a day basis and the dosage form provides less than about 25 percent incidence of headache as a side effect after single dose oral administration across a patient population.

In certain embodiments, the invention is further directed to a delayed release oral dosage form comprising tranexamic acid or pharmaceutically acceptable salt thereof and a delayed release material which provides for the delayed release of the tranexamic acid or pharmaceutically acceptable salt thereof from the dosage form such that the dosage form is suitable for administration on a two or three times a day basis and the dosage form provides less than about 10 percent incidence of nausea as a side effect when administered across a patient population, preferably less than about 7 percent incidence of nausea when administered across a patient population, more preferably less than about 5 percent incidence of nausea as a side effect when administered across a patient population, most preferably less than about 2 percent incidence of nausea as a side effect after single dose oral administration across a patient population.

In certain embodiments, the delayed release oral dosage form of the present invention provides less CNS side effects (e.g., headache), less GI side effects (e.g., nausea), or combination thereof in comparision to an equivalent amount of tranexamic acid or pharmaceutically acceptable salt thereof in an immediate release formulation when administered across a patient population. Additionally or alternatively, in certain embodiments the dosage form provides less CNS side effects (e.g., headache), less GI side effects (e.g., nausea), or combination thereof in comparision to a therapeutically equivalent amount of tranexamic acid administered intravenously in five minutes or less across a patient population.

In certain embodiments, the delayed release oral dosage form of the present invention provides for the reduction of at least one side effect as compared to an immediate release oral dosage form including an equivalent amount of tranexamic acid or pharmaceutically acceptable salt thereof, when the immediate release dosage form is administered across a same or different population of patients as said delayed release dosage form, and wherein said immediate release dosage form releases all of said tranexamic acid or pharmaceutically acceptable salt thereof within about 45 minutes when measured in vitro utilizing the USP 27 Dissolution Apparatus Type II Paddle Method @ 50 RPM in 900 ml water at 37±0.5° C. Such side effects can be for example, headache, nausea, and combinations thereof.

In certain embodiments, the present invention is directed to a delayed release oral dosage form comprising tranexamic acid or a pharmaceutically acceptable salt thereof and a delayed release material which provides for the delayed release of the tranexamic acid such that substantially none of said tranexamic acid is released from said dosage form after exposure of said dosage form for a period of 2 hours to an environmental fluid having a pH of less than about 2, preferably less than about 3, and substantially all of said tranexamic acid is released from said dosage form after exposure of said dosage form for a period of 1 hour to an environmental fluid having a pH of at least about 5, preferably at least about 6, more preferably at least about 7.

In certain embodiments, the present invention is directed to a delayed release oral dosage form comprising tranexamic acid or a pharmaceutically acceptable salt thereof and a delayed release material which provides for the delayed release of the tranexamic acid such that less than about 10% by weight, preferably less than about 5% by weight of said tranexamic acid is released from said dosage form after exposure of said dosage form for a period of 2 hours to an environmental fluid having a pH of less than about 2, preferably less than about 3, and at least about 75% by weight, preferably at least about 95% by weight of said tranexamic acid is released from said dosage form after exposure of said dosage form for a period of 1 hour to an environmental fluid having a pH of at least about 5, preferably at least about 6, more preferably at least about 7.

In certain preferred embodiments, the therapeutically effective dose of the tranexamic acid or pharmaceutically acceptable salt thereof is provided via the administration of two or more dosage units. For example, if the dosage unit comprises 650 mg of tranexamic acid or pharmaceutically acceptable salt thereof and the dose for administration is about 1300 mg then two dosage units would be administered to a patient in need of such treatment, or for example, when the dose for administration is 1950 mg, three dosage units would be administered.

In certain preferred embodiments, the invention is further directed to a method of treating a patient with one or more delayed release oral dosage forms comprising tranexamic acid or pharmaceutically acceptable salt thereof and a delayed release material, wherein the oral dosage form provides a therapeutically effective plasma level of tranexamic acid or pharmaceutically acceptable salt thereof in accordance with a three times a day (TID) dosing schedule, and the therapeutically effective dose administered comprises about 1300 mg of tranexamic acid or pharmaceutically acceptable salt thereof.

In certain preferred embodiments, the invention is further directed to a method of treating a patient with one or more delayed release oral dosage forms comprising tranexamic acid or pharmaceutically acceptable salt thereof and a delayed release material, wherein the oral dosage form provides a therapeutically effective plasma level of tranexamic acid or pharmaceutically acceptable salt thereof in accordance with a twice a day (BID) dosing schedule, and the therapeutically effective dose administered comprises about 1950 mg of tranexamic acid or pharmaceutically acceptable salt thereof.

In certain embodiments, the invention is directed to a method of providing a tranexamic acid plasma concentration within the range of about 5 mcg/mL to about 15 mcg/mL by administration of a delayed release formulation of the present invention comprising tranexamic acid or pharmaceutically acceptable salt thereof and a delayed release material on a three times a day basis to a patient in need of tranexamic acid or pharmaceutically acceptable salt thereof treatment.

In certain embodiments, the invention is further directed to a method of treating a human patient with heavy menstrual bleeding (e.g., menorrhagia) comprising administering about 1300 mg of tranexamic acid or pharmaceutically acceptable salt thereof on a three times a day basis to the human patient to provide a tranexamic acid or pharmaceutically acceptable salt thereof plasma concentration within the range of about 5 mcg/mL to about 15 mcg/mL after steady state oral administration to a human patient.

In certain embodiments, the invention is directed to a method of treating a patient suffering from menorrhagia, conization of the cervix, epistaxis, hyphema, hereditary angioneurotic edema, a patient with a blood coagulation disorder undergoing dental surgery, combinations thereof, and the like, by administering at least one dosage form of the present invention to the patient in need in tranexamic acid or pharmaceutically acceptable salt thereof therapy.

In certain embodiments, the modified release and/or delayed release material may be incorporated in a coating applied onto a tablet comprising the tranexamic acid or pharmaceutically acceptable salt thereof, or may be incorporated into a matrix with the tranexamic acid or pharmaceutically acceptable salt thereof, or a combination the two. For example, in certain preferred embodiments, the modified release material is a controlled release material such as a gel-forming or hydratable polymer which is added to a matrix composition comprising the tranexamic acid or pharmaceutically acceptable salt thereof.

In certain preferred embodiments, the delayed release oral dosage form comprises a core comprising tranexamic acid or a pharmaceutically acceptable salt thereof and a pharmaceutically acceptable excipient; and a delayed release material coated on the core which provides for the delayed release of the tranexamic acid or pharmaceutically acceptable salt thereof, such that the dosage form is suitable for administration on a two or three times a day basis.

In certain further preferred embodiments, the delayed release oral dosage form comprises a matrix comprising tranexamic acid or a pharmaceutically acceptable salt thereof and a delayed release material which provides for the delayed release of the tranexamic acid such that the dosage form is suitable for administration on a two or three times a day basis.

In certain preferred embodiments, the delayed release oral dosage form comprises a plurality of multiparticulates (e.g., inert beads, matrix multiparticulates, etc.) comprising tranexamic acid or a pharmaceutically acceptable salt thereof and a delayed release material which provides for the delayed release of the tranexamic acid or pharmaceutically acceptable salt thereof such that the dosage form is suitable for administration on a two or three times a day basis.

In certain embodiments, the tranexamic acid for use in the methods and formulations of the present invention is in the form of a pharmaceutically acceptable salt thereof. Such salt forms include for example and without limitation the sodium salt, potassium salt, calcium salt, magnesium salt and the like; as well as the hydrochloride, hydrobromide, sulfate, phosphate, formate, acetate, trifluoroacetate, maleate, tartrate, methanesulfonate, benzenesulfonate, p-toluenesulfonate-methanesulfonate salt forms, and the like. Preferably the active ingredient for use in accordance with the present invention is tranexamic acid.

An "immediate release oral dosage form" for purposes of the present invention is a dosage form which releases all of active ingredient (e.g., tranexamic acid) included therein within about 45 minutes when measured in vitro utilizing the USP 27 Dissolution Apparatus Type II Paddle Method @ 50 RPM in 900 ml water at 37±0.5° C.

The term "three times a day (TID) basis" for purposes of the present invention, means that the dosage regimen is to be administered three times a day, preferably on a schedule of every 8 hours.

The term "environmental fluid" is meant for purposes of the present invention to be an in-vitro dissolution fluid or gastrointestinal fluid.

DETAILED DESCRIPTION

The dosage regimen typically listed for tranexamic acid in HMB (Heavy Menstrual Bleeding) therapy is 1-1.5 g per dose administered three-four times a day at the onset of copious menstrual bleeding and continued for the first 3-5 days of the menstrual cycle. However, the most frequently reported dosage regimen of tranexamic acid is 1 g four times a day (4 g per day) for HMB therapy outside of the US. Knowledge of this common regimen is supported by a careful review of the randomized controlled trials published in the medical literature, product labeling from other countries' regulatory authorities having the product approved for HMB therapy, utilization data from Sweden (Rybo 1991), correspondence and interviews with non-US clinicians having experienced with the product, and this regimen is currently the dosage being studied by the US Center for Disease Control (CDC) in women with HMB associated with bleeding disorders.

In immediate release formulations the entire dose and the soluble components in the dosage form dissolve in gastrointestinal fluid and present a high concentration of solutes for absorption. The most frequently reported adverse effects are primarily confined to the proximal gastrointestinal tract (nausea and vomiting). These adverse symptoms appear to be related to the drug load presented to the gastric mucosa, since this effect can be minimized by reducing the immediate-release oral formulation dose or administering the product slowly by the intravenous route. In certain embodiments, a lower incidence of proximal gastrointestinal adverse effects is obtained with the preferred oral modified release formulation or delayed release formulation (e.g., dosed 1.3 g every 8 hours) of the invention, e.g., because of the modified or delayed release properties of the drug product formulation.

The modified release oral formulations of tranexamic acid of the present invention provides a release of the drug which is slower than that of the immediate release 500 mg Cyklokapron product current marketed in Canada which provided a mean release rate of 100% by weight tranexamic acid released by about 15 minutes when measured utilizing USP 27 Dissolution Apparatus Type II paddle method @ 50 RPM in 900 ml water at 37±0.5° C.

In accordance with the present invention a modified release tranexamic acid tablet for oral administration is disclosed. Preferably, the tablet contains at least one material (defined herein as any substance other than the active, i.e., tranexamic acid) which minimizes or eliminates the adverse gastrointestinal side effects in patients, for example, women dosed with oral tranexamic acid for treatment of menorrhagia.

A modified release product is defined by the United States Pharmacopeia (USP) as including delayed release products and extended-(controlled) release products. One embodiment is an extended release formulation, also called a sustained release formulation or a controlled release formulation. Extended, controlled, or sustained release formulations decrease the concentration of tranexamic acid and excipients dissolved in the stomach fluids after dosing by controllably releasing tranexamic acid over a period of time, as opposed to immediate release formulations which release the entire dose of tranexamic acid all at once. In immediate release formulations the entire dose and the soluble components in the dosage form dissolve in gastric fluid and present a high concentration of solutes for absorption.

Another embodiment is a delayed release formulation. The definition of a delayed release dosage form used herein is that from the USP, Chapter 1151 Pharmaceutical Dosage Forms—Tablets. In certain embodiments, where the delayed release formulation is a tablet, the tablet contains one or more coatings, intended to delay the release of tranexamic acid until the tablet has passed through the stomach (enteric coatings). A delayed release tablet is a dosage form that releases tranexamic acid at a time later than immediately after administration, that is, it exhibits a lag time in quantifiable plasma tranexamic concentrations. Preferably, one or more coating(s) delays the release of tranexamic acid until the dosage form has passed through the acidic medium of the stomach.

Delayed release formulations minimize or prevent release of tranexamic acid in the stomach and delay its release until the dosage form has emptied from the stomach into the small intestine. Delayed release formulations include enteric-coated tablets, enteric-coated capsules, enteric-coated granules, enteric-coated beads, and enteric-coated spheres (commonly referred to as "tiny little time pills" or multiparticulate dosage forms).

The enteric coating is stable under the acidic conditions in the stomach and releases tranexamic acid only in the less acidic or substantially neutral medium of the intestine, (e.g., at pH about 5.5 to about 7.5). It disintegrates, erodes, or dissolves, releasing tranexamic acid only when it encounters the higher pH of the intestine. Enteric-coated formulations substantially prevent dissolution of tranexamic acid in the relatively lower pH of the stomach. Both extended release and delayed release formulations are modified-release forms that thus minimize or prevent gastrointestinal reactions and side effects that occur when a dose of tranexamic acid reaches the stomach and unimpededly begins to dissolve.

As used herein, the terms extended release formulations, controlled release formulations, or sustained release formulations are used to describe drug product formulations designed to release tranexamic acid over a prolonged period of time. The definition of an extended release tablet used herein is that from the USP, Chapter 1151, as previously cited. The tablet is formulated in such a manner as to make tranexamic acid available over an extended period of time following ingestion. Expressions such as "prolonged action", "repeat-action", and "sustained release" also describe such a dosage form. Extended release dosage forms typically allow reduced dosing frequency as compared to when tranexamic acid is present in an immediate release dosage form. These extended release dosage forms may also reduce fluctuations in plasma tranexamic acid concentrations. Extended release dosage forms may be prepared as a tablet, capsule, granule, pellet or suspension, and may be packaged into capsules, sachets, etc. They may be prepared by any formulation technique where release of the active substance (tranexamic acid) from the dosage form is modified to occur at a slower rate than that from an immediate release product. In these formulations, tranexamic acid release occurs both in the stomach and intestine, but at a slower rate so that a bolus of dissolved drug does not reach the lining of the stomach or intestine and cause adverse effects, or adverse effects occur with a lower intensity or frequency because of the lower concentration of tranexamic acid. Hence, adverse effects are reduced, minimized or eliminated.

The modified release dosage forms of the present invention may be prepared as; tablets, capsules, granules, pellets, powders, dragees, troches, non-pariels, pills or encapsulated suspension, and may be packaged into capsules, sachets, etc. Such dosage forms may be prepared by any formulation technique where release of the active substance (tranexamic acid) from the dosage form is modified to occur at a slower rate than from an immediate release product. In these formulations, tranexamic acid release occurs in the stomach and/or intestine, but at a slower rate so that a bolus of dissolved drug does not reach the lining of the stomach and cause adverse effects, or adverse effects occur with a lower intensity or frequency because of the lower concentration of tranexamic acid. Hence, adverse effects are preferably reduced, minimized or eliminated.

Methods of preparing modified release formulations are known to one skilled in the art and are found in Modified Release Drug Delivery Technology, Rathbone, Hadgraft, and Roberts, Eds., Drugs and the Pharmaceutical Sciences, Vol. 126, Marcel Dekker Inc, New York, 2003; Modern Pharmaceutics, Third Edition, Banker and Rhodes, Eds., Drugs and the Pharmaceutical Sciences, Vol. 72, Marcel Dekker Inc., New York, 1996; Sustained and Controlled Release Drug Delivery Systems, Robinson, Ed., Drugs and the Pharmaceutical Sciences, Vol. 6, Marcel Dekker Inc., NY 1978; Sustained Release Medications, Chemical Technology Review No. 177, Johnson, Ed., Noyes Data Corporation 1980; Controlled Drug Delivery, Fundamentals and Applications, Second Edition, Robinson and Lee, Eds., Marcel Dekker Inc., New York, 1987, and as described in U.S. Pat. No. 6,548,084, which is expressly incorporated by reference herein in its entirety. The terms extended release formulation, controlled release formulation, and sustained release formulation are used interchangeably herein, unless indicated otherwise.

An extended release form, one example of a modified release form, makes tranexamic acid available over an extended period of time after ingestion. Extended release dosage forms coupled with the digestion process and the absorption process in the gastrointestinal tract cause a reduction in the amount of tranexamic acid in solution in the gastrointestinal tract compared to dosing tranexamic acid presented as a conventional dosage form (e.g., as a solution, or as an immediate release dosage form). The extended release formulation may be verified by in vitro dissolution testing and in vivo bioequivalence documentation, according to Food and Drug Administration standards, e.g, as set forth at www-.fda.gov, 21 CFR §314, 320, and also according to the USP. Briefly, in vitro dissolution is conducted on twelve individual dosage units. Multipoint dissolution profiles are obtained using discriminating combinations of apparatus, agitation speed, and medium. A surfactant may be used if justified. Sampling times are selected to define the release characteristics of the dosage form and to assure batch to batch reproducibility. Suitable equipment for dissolution testing is specified in USP 23 Apparatus 1 (rotating basket); Apparatus 2 (rotating paddle); Apparatus 3 (reciprocating cylinder*), Apparatus 4 (flow-through cell*); and Apparatus 5 (reciprocating disk*) (*modified testing conditions are used). Rotation speeds of 50 rpm, 100 rpm and 150 rpm are used with baskets, and 50 rpm, 75 rpm and 100 rpm are used with paddles. The temperature is 37° C.±0.5° C. The dissolution volume is 500 ml to 1000 ml. The dissolution medium is aqueous, at various pH values. The sampling schedule is such that adequate sampling is performed until either 80% of tranexamic acid is released or an asymptote is reached.

Tranexamic acid modified release tablets may be formulated to provide a dose of tranexamic acid, typically about 500 mg to about 2 grams from one to two tablets, within about the first one to two hours after the tablet is ingested. Thus, tranexamic acid release occurs at a designed rate over a period e.g., about 60 minutes to about 120 minutes. The rate of tranexamic acid release over this period of time is designed to provide a reduced concentration of tranexamic acid in the stomach while allowing the absorption of tranexamic acid to occur throughout the gastrointestinal tract. Absorption of tranexamic acid typically begins as soon as tranexamic acid is released from the dosage form and is dissolved in the gastrointestinal fluids contacting the membranes which line the gastrointestinal tract. The rate of release of tranexamic acid from the dosage form, the secretion of gastrointestinal fluid, and the absorption of drug by the gastrointestinal mucosa help to maintain low concentrations of drug in the gastrointestinal fluids. The lowered concentrations preferably result in lower intensity, frequency, and/or severity of gastrointestinal adverse side effects. The designed rate of release of tranexamic acid from the dosage form in the stomach and the upper small intestine, the natural emptying of gastric juice containing any dissolved tranexamic acid from the stomach, and the absorption of tranexamic acid from a larger segment of the gastrointestinal tract (i.e., both the stomach and the small intestine, rather than the stomach only or the lower portion of the small intestine if any modified release dosage form with a longer release time was used), preferably results in reduced levels of dissolved tranexamic acid in the region of the gastrointestinal tract proximal or distal to the dosage form. Reduced concentrations of tranexamic acid along the gastrointestinal tract preferably provide a reduction in adverse gastrointestinal effects associated with oral tranexamic acid therapy.

As used herein, alleviation of adverse effects using these formulations indicates any relief in one or more symptoms, such as decrease in incidence, severity, or duration of symptoms, and is not limited to absence of symptoms or elimination of symptoms. Thus, treatment includes any decrease in incidence, duration, intensity, frequency, etc. of adverse gastrointestinal symptoms including, but not limited to, headache, nausea, vomiting, diarrhea, constipation, cramping, bloating, and combinations thereof. The formulations may reduce symptoms at any time during tranexamic acid therapy, but minimized adverse effects are particularly noted immediately or shortly after dosing, that is, within the first few hours after dosing. As used herein, adverse gastrointestinal effects and side effects are used interchangeably to indicate nontherapeutic effects (i.e., not relating to any possible beneficial effects due to tranexamic acid), ranging from unpleasant but tolerable sensations to severe gastrointestinal symptoms. As used herein, the terms oral formulations, ingestable formulations, and orally administered formulations are used interchangeably and include any dosage forms which are ingested by mouth, including, but not limited to, tablets, pills, liquids, gelcaps, softgels, dragees, capsules, powders, granules, pellets, etc.

Modified release formulations of tranexamic acid include tablets, pellets, granules, capsules, or other oral dosage forms prepared in such a way to release tranexamic acid in a designed manner. In certain embodiments, the modified release material is a gel-forming polymer, a hydratable polymer, a water soluble polymer, a water swellable polymer, or mixtures thereof.

As used herein, the term delayed release formulation indicates any formulation technique where release of the active substance (tranexamic acid) from the dosage form is modified so that release occurs at a later time than that from a conventional immediate release product. One example of a delayed release formulation is an enteric coated formulation. Enteric coatings on the dosage form are intended to control the region of the gastrointestinal tract where dissolution and subsequent absorption of tranexamic acid from the enteric coated dosage form occurs. Enteric coatings can be prepared to substantially prevent dissolution of the dosage form contents in the stomach. These coatings function by incorporating materials in the enteric coating which allow the enteric coating to remain substantially intact in the acidic environment of the stomach. This substantially intact enteric coating minimizes or prevents the dissolution of tranexamic acid in stomach contents. Enteric coatings are formulated to release the contents of the dosage form when the pH of the gastrointestinal fluid increases. This increase in pH typically occurs when the dosage form passes out of the stomach into the small intestine. That is, the coating remains intact in the relatively more acidic stomach pH (pH<3) and disintegrates, dissolves, or is otherwise removed in the relatively less acidic pH of the intestine (pH of from about 3 through about 5 to about 7 for the upper regions of the small intestine and pH values from about 7 to about 8.5 in the lower regions of the intestines). Formulations can be prepared using enteric coatings intended to release tranexamic acid at pH values of about 5.5 to about 6.5 or at higher pH values that typically occur in the lower regions of the intestines. In those delayed release formulations intended to dissolve at pH 5.5 to about 6.5 or higher, tranexamic acid release occurs substantially only upon reaching the duodenum (the upper portion of the small intestine) so that substantially no tranexamic acid is released in the stomach, thus minimizing or eliminating adverse effects.

Tranexamic acid formulated as delayed release tablets may contain an enteric coating which disintegrates, dissolves, or erodes at neutral or slightly acidic or slightly alkaline pH, and thereby allows dissolution of tranexamic acid upon leaving the stomach, that is, upon stomach emptying into the small intestine. The release of tranexamic acid in the intestine reduces gastrointestinal side effects associated with the large dose of tranexamic acid quickly released into the stomach. Patients treated with enteric coated formulations of tranexamic acid for delayed release should be cautioned to not consume antacids while under tranexamic therapy, because antacids will change the stomach pH and thus alter the site of tablet dissolution or disintegration. Other types of delayed release formulations are available, and the above example is not limiting.

A delayed release form, another example of a modified release form, makes tranexamic acid available at a time other than immediately following oral administration. As for extended release formulations, delayed release formulations may be verified by in vitro dissolution testing and in vivo bioequivalence documentation according to the standard available as previously set forth (USP). When the guidance refers to dissolution testing in addition to application/compendial release requirements, the dissolution test should be performed in 0.1 N HCl for two hours (acid stage), followed by testing in USP buffer media at a pH range between 4.5 to 7.5 (buffer stage) under standard (application/compendial) test conditions and increased agitation speeds using the application/compendial test apparatus. For the rotating basket method (Apparatus 1) a rotation speed of 50 rpm, 100 rpm, and 150 rpm may be used, and for the rotating paddle method (Apparatus 2) a rotation speed of 50 rpm, 75 rpm, and 100 rpm may be used. Multipoint dissolution profiles may be obtained during the buffer stage of testing. Adequate sampling should be performed, e.g., at 15 min, 30 min, 45 min, 60 min, 120 min (following the time from which the dosage form is placed in the buffer), until either 80% of the drug is released or an asymptote is reached.

Methods of preparing delayed release formulations are known to one skilled in the art and are found in, for example, Remington's Pharmaceutical Sciences 16$^{th}$ Edition, Mack Publishing Company 1980, and the references cited for extended release formulations.

Delayed release formulations may be enteric coated tranexamic acid tablets or enteric coated granules. These tablets may be prepared by coating compressed tablets with a delayed release material such as a commercial or specially formulated enteric film coat, for example, a wax, a polymer, and/or other additives such as colorants and pigments that form a pH-sensitive matrix that meets (USP) and Food and Drug Administration (FDA) requirements for enteric coated tablets. The enteric coating permits disintegration of the tranexamic acid tablets and dissolution of tranexamic acid as a result of the pH change between the stomach and the duodenum. Tablet excipients, such as delayed release materials, which inhibit rapid release of tranexamic acid in the stomach and which promote dissolution and release in the intestine may also be used. These include, but are not limited to, phthalic acid derivatives such as phthalic acid derivatives of vinyl polymers and copolymers, hydroxyalkylcelluloses, alkylcelluloses, cellulose acetates, hydroxyalkylcellulose acetates, cellulose ethers, alkylcellulose acetates and partial esters thereof, and polymers and copolymers of lower alkyl acrylic acids and lower alkyl acrylates and partial esters thereof. Commercial preparations intended for the enteric coating of tablets, capsules, and granules are available from Degussa (Parsippany, N.J.) and Colorcon (West Point, Pa.). In one embodiment, the polymers are methacrylic acid copolymers. These are copolymers of methacrylic acid with neutral acrylate or methacrylate esters such as ethyl acrylate or methyl methacrylate, for example, methacrylic acid copolymer, Type C, USP (a copolymer of methacrylic acid and ethyl acrylate having between 46.0% and 50.6% methacrylic acid units), commercially available from Rohm Pharma as Eudragit® L 100-55 (as a powder) or L30D-55 (as a 30% dispersion in water). In another embodiment, the polymers are hydroxypropyl cellulose phthalate, hydroxypropyl methylcellulose phthalate, cellulose acetate phthalate, polyvinylacetate phthalate, polyvinylpyrrolidone phthalate, and the like. One or more pH-dependent excipient(s) are present in amounts ranging from about 1% by weight to about 20% by weight, from about 5% by weight to about 12% by weight, or in an amount of about 10% by weight.

The quantity of pH dependent excipients is sufficient to produce a delayed release formulation from which the release rate of tranexamic acid is controlled such that at a pH below about 5 the rate of dissolution is significantly retarded. For methacrylic acid copolymer, type C, USP (Eudragit® L 100-55), a quantity of pH dependent polymer coating may be applied to tablets in the range between about 2% to about 15% by weight (dry basis). In another embodiment, the range is between about 3% to about 6% by weight (dry basis). The pH dependent polymer may have from about 1% to about 20% of the methacrylic acid carboxyl groups neutralized. In one embodiment about 3% to about 6% of the binder methacrylic acid carboxyl groups are neutralized. One or more pH independent excipients may be present in amounts ranging from about 1% by weight to about 10% by weight, from about 1% by weight to about 3% by weight, or in an amount of about 2% by weight. Film-forming or viscosity enhancing agents may also be present, such as hydroxypropyl methylcellulose, hydroxypropyl cellulose, methylcellulose, polyvinylpyrrolidone, neutral poly(meth)acrylate esters, and the like.

Excipients may be admixed so as to form a homogeneous mixture with tranexamic acid and the pH dependent binder. Excipients include pH independent binders or film-forming agents such as hydroxypropyl methylcellulose, hydroxypropyl cellulose, methylcellulose, polyvinylpyrrolidone, neutral poly(meth)acrylate esters (e.g., the methyl methacrylate/ethyl acrylate copolymers sold as Eudragit® (Rohm Pharma), starches, gelatin, sugars such as glucose, sucrose, and mannitol, silicic acid, carboxymethylcellulose, and the like, diluents such as lactose, mannitol, dry starch, microcrystalline cellulose and the like, surface active agents such as polyoxyethylene sorbitan esters, sorbitan ethers, and the like, coloring agents, flavoring agents, lubricants such as talc, calcium stearate, and magnesium stearate, solid polyethylene glycols, sodium lauryl sulfate, and other tableting aids. These excipients may be combined with tranexamic acid to form delayed release tablets.

In certain embodiments of the formulation includes tranexamic acid in the range of about 50% by weight to about 95% or more by weight of the formulation. In other embodiments, tranexamic acid is in the range of about 60% by weight to about 90% by weight, or about 60% by weight to about 80% by weight of the formulation. The remaining weigh may be made up of the modified release material and additional excipients.

In certain embodiments, the pH dependent binder may be in the range of about 5% by weight to about 40% by weight, about 5% by weight to about 25% by weight, or about 5% by weight to about 15% by weight. The remaining weight may be made up of tranexamic acid, pH independent binders, fillers, or other excipients.

To prepare delayed release tablet formulations, the agent to control or delay the release of tranexamic acid may be incorporated into the tablet matrix or coated onto the tablet surface or both. Tablet formulations prepared with the pH dependent excipient added as a binder in the tablet matrix are formulated by granulating a blend of powders composed with the pH dependent binder. Alternatively, the pH dependent binder may be added as a powder and wet granulated by addition of a solvent to the powder blend. The powder blend is formed by combining portions of the powdered components that make up the tablet. These powders are intimately mixed by dry-blending. The dry blended mixture is granulated by wet mixing of a solution of a binding agent with the powder blend. The time for such wet mixing may be controlled to influence the dissolution rate of the formulation. For example, the total powder mix time, that is, the time during which the powder is granulated, may range from about 1 min to about 10 min, or from about 2 min to about 5 min. Following granulation, the particles are removed from the granulator and placed in a fluid bed dryer, a vacuum dryer, a microwave dryer, or a tray dryer for drying. Drying conditions are sufficient to remove unwanted granulating solvent, typically water, or to reduce the amount of granulating solvent to an acceptable level. Drying conditions in a fluid bed dryer or tray dryer are typically about 60° C. The granulate is dried, screened, mixed with additional excipients such as disintegrating agents, flow agents, or compression aids and lubricants such as talc, stearic acid, or magnesium stearate, and compressed into tablets.

The tablet that contains a delayed release agent within the tablet matrix may be coated with an optional film-forming agent. This applied film may aid in identification, mask an unpleasant taste, allow desired colors and surface appearance, provide enhanced elegance, aid in swallowing, aid in enteric coating, etc. The amount of film-forming agent may be in the range of about 2% tablet weight to about 4% tablet weight. Suitable film-forming agents are known to one skilled in the art and include hydroxypropyl cellulose, cellulose ester, cellulose ether, one or more acrylic polymer(s), hydroxypropyl methylcellulose, cationic methacrylate copolymers (diethylaminoethyl) methacrylate/methyl-butyl-met-hacrylate copolymers such as Eudragit E® (Rohm Pharma) and the like. The film-forming agents may optionally contain colorants, plasticizers, fillers, etc. including, but not limited to, propylene glycol, sorbitan monooleate, sorbic acid, titanium dioxide, and one or more pharmaceutically acceptable dye(s).

In certain embodiments, the tranexamic acid tablets of the invention are coated with a modified release material. In certain embodiments, tranexamic acid tablets are formulated by dry blending, rotary compacting, or wet granulating powders composed of tranexamic acid and tablet excipients. These powders are compressed into an immediate release tablet. Coating this immediate release tablet with a modified release material as described herein renders this tranexamic acid tablet as a modified release tablet.

In addition to the modified release material and/or delayed release material, the formulations of the invention may also contain suitable quantities of other materials, e.g. preservatives, diluents (e.g., microcrystalline cellulose), lubricants (e.g., stearic acid, magnesium stearate, and the like), binders (e.g., povidone, starch, and the like), disintegrants (e.g, croscarmellose sodium, corn starch, and the like), glidants (e.g., talc, colloidal silicon dioxide, and the like), granulating aids, colorants, and flavorants that are conventional in the pharmaceutical art. Specific examples of pharmaceutically acceptable excipients that may be used to formulate oral dosage forms are described in the Handbook of Pharmaceutical Excipients, American Pharmaceutical Association (2003), incorporated by reference herein.

In one embodiment, tranexamic acid tablets are coated with an enteric film coat. Tranexamic acid tablets are formulated by dry blending, rotary compacting, or wet granulating powders composed of tranexamic acid and tablet excipients. These powders are compressed into an immediate release tablet. Coating this immediate release tablet with an enteric coating renders this tranexamic acid tablet as a delayed release tablet.

Extended release formulations of tranexamic acid include tablets, pellets, granules, capsules, or other oral dosage forms prepared in such a way to release tranexamic acid in a controlled manner.

Extended release tranexamic acid tablets are prepared by adding a gel-forming or hydratable polymer to a tranexamic tablet composition. Suitable gel-forming or hydratable polymers include, but are not limited to, hydroxypropylcellulose, hydroxypropylmethylcellulose, carboxymethylcellulose, polyvinyl alcohol, etc. This provides a compressed tablet that may or may not be film-coated. The tablet releases tranexamic acid by diffusion of tranexamic acid through the tablet matrix, or by erosion of the tablet matrix, or by a combination of diffusion from and erosion of the tablet matrix. Alternatively, water-swellable polymers may be used to form the tablet matrix. Tablets formed with water swellable polymers release tranexamic acid by diffusion of tranexamic acid through the tablet matrix, or by erosion of the tablet matrix, or by a combination of diffusion from and erosion of the tablet matrix. One or more water-soluble hydrophilic polymer(s) may also be used. These include polyvinylpyrrolidine, hydroxypropyl cellulose, hydroxypropylmethylcellulose, now referred to as hypromellose (e.g., Methocel™, Dow Chemical Company), methyl cellulose, vinyl acetate/crotonic acid copolymers, methacrylic acid copolymers, maleic anhydride/methyl vinyl ether copolymers, derivatives thereof and mixtures thereof. In various embodiments, the polymer is hydroxypropyl cellulose or hydroxypropylmethylcellulose. The polymer may be hydroxypropyl-methyl cellulose with a viscosity ranging from about 50 cps to about 200 cps. The polymer may be hydroxypropylmethylcellulose with a viscosity of 100 cps, commercially available as Methocel™ K 100 LV (Dow Chemical Company). The amount of polymer in the composition may be in the range of about 5% by weight to about 50% by weight of the composition. In various embodiments, the polymer is in the range of about 10% by weight to about 35% by weight of the composition, or about 10% by weight to about 30% by weight of the composition.

The tablet matrix may also contain soluble and insoluble components to aid in the formulation and/or the extended release rate of tranexamic acid. The release process may be adjusted by varying the type, amount, and the ratio of the tablet ingredients to produce the desired dissolution profile, as known to one skilled in the art. A coating may be a partially neutralized pH-dependent binder that controls the rate of tranexamic acid dissolution in aqueous media across the range of pH in the stomach, which has a pH of about 2, and the intestine, which has a pH of about 5.5. One or more pH dependent binders are used to control the dissolution profile so that tranexamic acid is released slowly and continuously as the formulation passes through the stomach and gastrointestinal tract.

In one embodiment, compressed extended release tablets are formulated to comply with USP criteria and to be of such a size and shape to be easy to swallow. The size of the tablet will depend upon the dose of tranexamic acid that is needed to provide adequate therapy and the particular formulation and excipients that are selected to provide the physical properties necessary for tableting and for extended release. In various embodiments, a compressed extended release tablet contains from about 500 mg to about 1 gram of tranexamic acid, or from about 600 mg to about 750 mg of tranexamic acid. The daily dose of tranexamic acid may be achieved by taking one or two tablets at each dosing time.

In certain embodiments, the tranexamic acid included in the dosage form is from about 375 mg to about 1500 mg, preferably from about 375 mg to about 1000 mg. In one embodiment, the dose of tranexamic acid per tablet is in the range of about 500 mg to about 1000 mg for tablets and from about 500 mg to about 1500 mg for a sachet filled with granules. In another embodiment, the dose of tranexamic acid is in the range of about 3 grams/day to about 6 grams/day in three or four divided doses. As an example, a total daily dose of 3 grams tranexamic acid may be divided into three doses of one tablet each with each tablet containing 1 gram tranexamic acid, or may be divided into four doses of one tablet each with each tablet containing 0.75 gram tranexamic acid. As another example, a total daily dose of 4 gram tranexamic acid may be divided into three doses of two tablets at each dose with each tablet containing 0.666 gram tranexamic acid, or may be divided into four doses of one tablet each with each tablet containing 1 gram tranexamic acid. As another example, a total daily dose of 5 gram tranexamic acid may be divided into three doses of one tablet each with each tablet containing 1.66 gram tranexamic acid, or may be divided into four doses of two tablets each with each tablet containing 0.625 gram tranexamic acid. As another example, a total daily dose of 6 gram tranexamic acid may be divided into three doses of two tablets each with each tablet containing 1 gram tranexamic acid, or may be divided into four doses of two tablets each with each tablet containing 0.75 gram tranexamic acid. For ease of swallowing, the dose of tranexamic acid taken at each dosing time may be delivered by taking multiple tablets. For example, the 4 gram daily dose may be delivered by taking two 666.67 mg tablets three times a day or two 500 mg tablets four times a day. Similarly, the 3 gram daily dose may be achieved by taking two 550 mg tablets three times a day or two 375 mg tablets four times a day. Alternatively, for ease of reference, a dose of 600 mg, 650 mg, or 700 mg of tranexamic acid per tablet may be used. In a preferred embodiment, a total daily dose of 3900 mg/day is administered in three divided doses of 1300 mg of two tablets at each dose with each tablet containing 650 mg of tranexamic acid. Alternatively, each dose may be delivered by taking granules containing the prescribed amount of tranexamic acid presented in a convenient unit dose package. Such examples are not limiting and other doses within these ranges will be appreciated by those skilled in the art.

Alternatively, extended release or delayed release tranexamic acid formulations may be administered as a multiparticulate formulation (e.g., by pellets or granules in a sachet). Extended release tranexamic acid pellets or granules may be prepared by using excipients to control the release of tranexamic acid from the granule or pellet matrix. Extended release preparations may also be formulated using coatings to control the release of tranexamic acid from the granule or pellet. Delayed release formulations may be prepared by incorporating excipients to control the release of tranexamic acid in the matrix of the granule or pellet, or as coating materials on the surface of the granule or pellet. U.S. Pat. No. 6,433,215, which is expressly incorporated by reference herein in its entirety, discloses a method of building layers of drug and binder on sugar spheres and coating them with a membrane to form a film coating. Such a coating may be used for either an extended release formulation or a delayed release formulation, and/or for pharmaceutical elegance. U.S. Pat. Nos. 5,650,174; 5,229,135; and 5,242,337, each of which is expressly incorporated by reference herein in its entirety, disclose variations on fabricating a pellet or nonpareil dosage form. Spheres are filled into packets, termed sachets, which are filled by weight to contain the prescribed dose of drug. Multiparticulates may be coated with an extended release coating or a delayed release coating, as disclosed in U.S. Pat. No. 6,066,339, which is expressly incorporated by reference herein in its entirety. Coated multiparticulates may be packaged in capsules or sachets. The formulation of granules or pellets for extended or delayed release is described in Multiparticulate Oral Drug Delivery, Ghebre-Sellassie, Ed. in Drugs and the Pharmaceutical Sciences, Vol. 65, Marcel Dekker Inc., NY, 1994 and in the relevant parts of the references for extended release formulations and delayed release formulations previously cited and the relevant portions incorporated herein by reference. In certain embodiments the multiparticulates are incorporated into a capsule or are formed into a tablet (e.g., such as by compression with additional excipients).

The inventive tranexamic acid formulations may be used for additional indications other than menorrhagia.

The invention will be further appreciated with respect to the following examples.

EXAMPLE 1

A sustained release formulation includes pH-dependent and -independent binders. Tranexamic acid (5333 g) is combined with methacrylic acid copolymer, Type C (Eudragit® L 100-55 (Rohm Pharma) (200 g), microcrystalline cellulose (Avicel® (142 g), and polyvinyl pyrrolidone powders (20 g) and intimately mixed in a Fielder PMA 65 mixer-granulator. The mixture is granulated with a solution of sodium hydroxide (8 g) in water, and a 30% aqueous dispersion of methyl methacrylate/ethyl acrylate copolymer (Eudragit® NE 30 D (Rohm Pharma) (300 g) is added to the wet mass. The resulting granulate is dried in an Aeromatic Strea-5 fluid bed drier, screened, and then mixed with croscarmellose sodium (10 g) and magnesium stearate (10 g). The mixture is compressed into tablets with a Manesty B tablet press to achieve a dose of 700 mg tranexamic acid per tablet.

EXAMPLE 2

A sustained release formulation is prepared according to Example 1 except that Eudragit® L 100-55 is reduced to 100 g, and Eudragit® NE 30 D is replaced by a 40% aqueous dispersion of a methyl methacrylate/ethyl acrylate copolymer (Eudragit® NE 40 D (Rohm Pharma) 200 g).

EXAMPLE 3

A sustained release formulation is prepared by blending tranexamic acid 700 mg/tablet with microcrystalline cellulose and polyvinylpyrrolidine K25, granulating with water, drying, and blending with croscarmellose sodium and magnesium stearate. The blend is compressed into tablets and coated with an enteric coating.

EXAMPLE 4

An extended release composition is prepared by mixing tranexamic acid (3000 g) and from about 100 g to about 300 g Methocel™ K 100 LV (Dow Chemical Company). The mixture is dry blended, and then is granulated using water until proper granulation is obtained, as known to one skilled in the art. Wet granules are dried in a fluid bed dryer, sifted, and ground to appropriate size. Lubricating and flow agents are mixed with the dried granulation to obtain a final formulation which is compressed into tablets containing 650 mg of tranexamic acid per tablet.

EXAMPLE 5

In Example 5, modified release formulations are prepared.

Methocel™ K 100 LV (Dow Chemical Company) is loaded into a mixer and dry blended with tranexamic acid. The mixture is granulated using water until proper granulation is obtained, as known to one skilled in the art. The granulation is then dried, sifted, and ground to appropriate size.

Talc and magnesium stearate are screened and blended with dry granulation. The granulation is loaded into a hopper and compressed into tablets. Tablets are then coated with an aqueous film coating.

In the following formulations, 650 mg tranexamic acid tablets are compressed from the granulation with water added up to the desired quantity (qs) to form the desired granulation then substantially removed by drying.

Formulation one contains 50 mg/tablet Methocel™ K 100 LV Premium CR Grade (Dow Chemical Company), 50 mg/tablet lactose monohydrate, 25 mg/tablet USP talc, and 8 mg/tablet magnesium stearate.

Formulation two contains 75 mg/tablet Methocel™ K 100 LV Premium CR Grade (Dow Chemical Company), 50 mg/tablet lactose monohydrate, 25 mg/tablet USP talc, and 10 mg/tablet magnesium stearate.

Formulation three contains 100 mg/tablet Methocel™ K 100 LV Premium CR Grade (Dow Chemical Company), 50 mg/tablet lactose monohydrate, 30 mg/tablet USP talc, and 10 mg/tablet magnesium stearate.

EXAMPLE 6

Modified release 650 mg tranexamic acid tablets were prepared having the ingredients listed in the Table 1 below:

TABLE 1

| Ingredient | Quantity per batch (kg) | Quantity per tablet (mg) |
| --- | --- | --- |
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |

*Purified water is removed during processing

The formulation of Example 6 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the hypromellose USP Methocel K3 Premium to the V-blender. Blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets to desired weight.

EXAMPLE 7

In Example 7, immediate release 650 mg tranexamic acid tablets were prepared having the ingredients listed in Table 2 below:

TABLE 2

| Ingredient | Quantity per batch (kg) | Quantity per tablet (mg) |
| --- | --- | --- |
| Active Ingredient | | |
| Tranexamic Acid, EP (650 mg/tab) | 84.50 | 650.0 |
| Inactive Ingredients | | |
| Microcrystalline Cellulose, NF (Avicel PH 101) | 5.753 | 44.25 |
| Microcrystalline Cellulose, NF (Avicel PH 102) | 10.660 | 82.00 |
| Colloidal Silicon Dioxide, NF | 0.0975 | 0.75 |
| Pregelatinized Corn Starch, NF | 6.435 | 49.50 |
| Croscarmellose Sodium, NF | 1.950 | 15.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water, USP* | 17.550 | 135.00 |
| Film Coating (Inactive Ingredients)** | | |
| Opadry White YS-1-7003 | 4.110 | — |
| Purified Water, USP | 36.990 | — |

*Purified water is removed during processing
**6 kg excess prepared to account for losses during transfer The formulation of Example 7 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the croscarmellose sodium and MCC to the V-Blender and blend.
10. Pass magnesium stearate and stearic acid through oscillating granulator equipped with a #40 mesh screen. Add magnesium stearate and stearic acid to the V-blender and blend.

11. Perform specified physical property testing. Proceed to compression.
12. Compress tablets.
13. After compression, spray coat the compressed dosage forms with the Opadry White in water.

EXAMPLE 8

In Example 8, modified release 650 mg tranexamic acid tablets were prepared as in Example 6 and coated with film coating similar to the immediate release tablets of Example 7. The ingredients are listed in Table 3 below:

TABLE 3

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |
| Film Coating (Inactive Ingredients)** | | |
| Opadry White YS-1-7003 | 4.305 | — |
| Purified Water, USP | 38.750 | — |

*Purified water is removed during processing
**6 kg excess prepared to account for losses during transfer

EXAMPLE 9

In Example 9, 650 mg delayed release tranexamic acid tablets were prepared having the ingredients listed in Table 4 below:

TABLE 4

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose, NF (Avicel PH 101) | 5.753 | 44.25 |
| Microcrystalline Cellulose, NF (Avicel PH 102) | 10.660 | 82.00 |
| Colloidal Silicon Dioxide, NF | 0.0975 | 0.75 |
| Pregelatinized Corn Starch, NF | 6.435 | 49.50 |
| Croscarmellose Sodium, NF | 1.950 | 15.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water, USP* | 17.550 | 135.00 |
| Film Coating (Inactive Ingredients)** | | |
| Acryl-Eze (93018359) | 12.900 | — |
| Silicone Emulsion, 30% | 0.323 | — |
| Purified Water, USP | 51.271 | — |

*Purified water is removed during processing; mg per tablet is based on a theoretical specific gravity of 1.0 g/ml
**6 kg excess prepared to account for losses during transfer The formulation of Example 9 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the croscarmellose sodium and MCC to the V-Blender and blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets.
13. After compression, spray coat the compressed dosage forms with the film coating.

EXAMPLE 10

Delayed Release Tablets with Enteric Coating

In Example 10, 650 mg delayed release tranexamic acid tablets are prepared having the ingredients listed in Table 5 below:

TABLE 5

| Ingredient | Quantity per batch (kg) | Quantity per tablet (mg) | % |
|---|---|---|---|
| Tranexamic Acid Tablets - Quantitative Composition | | | |
| Tranexamic Acid, EP | 84.50 | 650 | 72.2% |
| Microcrystalline Cellulose, NF | 16.41 | 126.25 | 14.0% |
| Colloidal Silicon Dioxide, NF | 0.10 | 0.75 | 0.1% |
| Pregelatinized Corn Starch, NF | 6.44 | 49.5 | 5.5% |
| Croscarmellose Sodium, NF | 1.95 | 15 | 1.7% |
| Povidone, USP | 4.68 | 36 | 4.0% |
| Stearic Acid, NF | 2.34 | 18 | 2.0% |
| Magnesium Stearate, NF | 0.59 | 4.5 | 0.5% |
| Purified Water[1], USP | 17.55 | 135 | |
| Sub-total | 117.00 | 900 | 100.0% |
| Sub-coating composition | | 2 to 3% weight gain | |
| Opadry | | 18 to 27 | |
| Purified Water[1], USP | | — | |
| Enteric Film Coating Composition | | 2 to 3% weight gain | |
| Acryl-Eze | | 180 to 220 | |
| Silicone Emulsion | | 0.2 to 0.3 | |
| Purified Water[1], USP | | | |

[1]Purified water is removed during processing.

The formulation of Example 10 is prepared as follows:
Tranexamic acid, pregelatinized corn starch, colloidal silicon dioxide and a portion of the microcrystalline cellulose (5%) are blended in a high shear blender and granulated with a solution of povidone in water. The granulation is dried in a fluid bed drier or a tray drier to a moisture content of approximately 1.2%. The dried granulation is sized through a suitable comminutor such as an oscillating granulator equipped with a 30 mesh screen and added to a V blender. Croscarmellose and the remaining portion (9%) of the microcrystalline cellulose are added to the blender and mixed until uniform. Magnesium stearate and stearic acid are sieved to remove lumps, added to the blender, and blended for approximately 3 minutes. The lubricated granulation is compressed into suitable tablets such as capsule shaped tablets using punches and a dye on a rotary tablet press.

Thereafter, the tablets are coated with a suitable sub-coating to separate the acidic tablet core from the acid sensitive enteric coating using a suitable film forming formulation such as Opadry. Alternatively, comparable sub-coatings may be applied using Spectrablend or a sub-coating formulated with hydroxypropylmethylcellulose and one or more plasticizers. Pigments may be added to the sub-coat to enhance tablet appearance. This coating is typically performed in a rotating coating pan such as an Accelacoater with a spray gun arrangement and heated air.

An enteric coating is then applied in a similar manner as the sub-coating using enteric coating formulations such as Acyl-Eze, Sureteric, or Eudragit L30D, Hydroxypropylmethylcellulose Phthalate (HP-55, Shin-Etsu), Aquateric (FMC), or Eudragit L100-55 (Röhm Pharma). The amount of applied solids needed to protect the tablet from disintegration/dissolution in acid varies with tablet weight and geometry but is typically in the range of about 3 to about 10%.

Alternatively, acceptable tablets can be prepared without a subcoat by applying the enteric film coat directly onto the tablet surface.

EXAMPLE 11

Delayed Release Enteric Coated Tablets Using Fluid Bed Technology

In Example 11, tranexamic acid tablets are prepared in accordance with Example 10 and are coated with an Enteric film coat listed in Table 6 below:

TABLE 6

| Enteric Film Coating Composition | % |
|---|---|
| Aquateric | 11 |
| Tween 80 | 0.1 |
| Triacetin | 3.9 |
| Purified Water[1], USP | 85 |

[1]Purified water is removed during processing.

The coated tranexamic acid tablets of Example 11 are prepared as follows:

A sub-coating of hydroxypropylmethylcellulose can be applied to the tranexamic acid tablets as noted in Example 10. Alternatively, an enteric coating may be applied without a subcoat by film coating directly onto the tablet.

In Example 11, the enteric film coating composition is applied using a fluid bed coating technique with equipment such as a Glatt fluid bed coater configured for film coating or an Aeromatic fluid bed coating. Tablets are charged into the fluid bed coater and suspended in a rapidly moving heated air stream. The coating suspension is sprayed onto the tablets and the water evaporated by the heated air. Additional drying of the coated tablets may be preformed by stopping the spray and continuing the flow of heated air. Monitoring of air flow rates, influent and effluent temperatures, humidity levels, flow rates for the coating solution, and atomizing air pressure assures that this coating process is controlled and reproducible. The amount of applied solids needed to protect the tablet from disintegration/dissolution in acid varies with tablet weight and geometry but is typically in the range of about 3 to about 10%.

EXAMPLE 12

Delayed Release Formulations Utilizing Extrusion—Spheronization

In Example 12 delayed release formulations are prepared. In Example 12, Tranexamic acid pellets or "tiny little time pills" are formulated, enteric coated, and filled into capsules or sachets.

The ingredients for inclusion in the pellets is listed in Table 7 below:

TABLE 7

| Raw Material | 1 KG Batch Grams | % |
|---|---|---|
| Tranexamic Acid | 500 | 50% |
| Avicel ® RC-581 | 500 | 50% |
| Purified Water[1] | 1 liter | |
| Total | | 100.0% |

[1]Removed during processing

The tranexamic acid pellets of Example 12 are prepared as follows:

Tranexamic acid and Avicel RC-581 are granulated in a high shear granulator with purified water. The wet granulated powders are transferred into an extruder and extruded through a plate or screen to produce small pellets or strings. The pellets/strings are then transferred into a spheronizer which is a chamber with a rotating plate in the bottom. The pellets are spun around for a short period of time which turns the pellets into spheres. The spheres are then dried to a moisture content of about 5%. Spheroids with size ranges between 250µ and 850µ (20/60 mesh size) are obtained by sieving. The spheroids outside of this desired range are discarded or ground and added to future batches. This process produces a very spherical, durable granule. Extrusion/spheronization equipment is produced by Vector/Freund or Niro.

Tranexamic acid spheroids are then coated with enteric coating polymers with or without a sub-coat as described Examples 10 and 11.

The coated spheroids can be filled into gelatin capsules or sachets. The proper dose to be filled in capsules may be determined by the desired capsule size and the fill weight. For example, a 650 mg dose can be obtained by taking two capsules each containing 350 mg of tranexamic acid. Sachet dosing forms are convenient because the desired dose can be added to foods such as applesauce, puddings, juices, drinks, milk, etc.

EXAMPLE 13

Delayed Release Formulation Utilizing Coated Nonpareils

In Example 13 delayed release formulations utilizing beads coated with tranexamic acid are prepared. The ingredients for inclusion in the coated nonpareil beads are listed in Table 13, below.

TABLE 8

| Components | Quantities used (kg) | | | |
|---|---|---|---|---|
| | Laboratory Pan | Pilot Pan | Semi-ind. Pan | Formula (%) |
| Nonpareils | 0.832 | 6.658 | 46.60 | 42.62 |
| Tranexamic Acid | 1.000 | 8.000 | 56.00 | 51.22 |
| PVP K30 | 0.048 | 0.382 | 2.70 ± (80%) | 2.45 |
| Talc | 0.072 | 0.580 | 4.06 | 3.71 |

(Ethanol/Purified Water) removed during processing

This coating is performed in a pan with heated air to dry the coating solution. The beads are prepared as follows:

One kilogram of nonpareils having a size of approximately 800 microns is introduced into a laboratory-size solid pan of about 5 to 10 liters. A 20% ethanolic solution of polyvinylpyrrolidone K30 is sprayed onto the non-pareils in order to wet the surface of the nonpareils and make them slightly sticky.

Tranexamic acid is milled and sieved to a particle size of approximately 600 microns. Tranexamic acid powder is dusted onto the bed of sticky nonpareil cores that are rotating in a pan. Talc may be introduced into the bed of cores in the event of sticking. The first cycle is terminated after a short drying period with heated air which allows tranexamic acid to adhere to the core.

The cycles are thus repeated in succession until all of the tranexamic acid is coated onto the cores. To build up the cores properly, about 1/30th of the ethanolic solution and about 1/25th of the tranexamic acid are added at each cycle.

After all of the tranexamic acid has been added, the remaining proportion of the talc is deposited at the surface of the beads with the aid of the solution PVP K30 in order to isolate the tranexamic acid from surface erosion and external treatments.

The beads are further dried in the pan or in a drying oven or fluid bed drier to a low moisture content of approximately 1 to 3%.

This manufacture of tranexamic acid nonpareils can be carried out in a pilot- or semi-industrial-size pan. The procedure remains the same except that the quantities of materials are proportionately increased based on the capacity of the equipment. Care is taken by people skilled in the art to adjust the amount of solution and tranexamic powder added in each cycle so that the beads can be formed without undue sticking, twining, or aggregation and the beads formed are suitable for further processing.

The tranexamic acid beads can be coated, with or without a seal coat, using the formulations and procedures described above for tranexamic acid tablets. Because of the larger surface area for the beads, the total amount of coating added is increased proportionately. Coating amounts of about 20% to about 30% may be added to provide proper protection against dissolution in acidic solutions.

A convenient dosing unit of enteric coated tranexamic acid beads can be obtained by encapsulating the beads in gelatin capsules or packaging the beads in sachets. The proper dose of tranexamic acid to be taken at each dosage period is achieved by proper selection of the capsule size and or the number of capsules to be taken at each dosing period. Sachets containing the desired dose of enteric coated tranexamic acid beads can be added to foods such as applesauce or pudding, sprinkled on salads or other solid foods, or dispersed in juices or milk.

EXAMPLE 14

Adverse Events from Bioavailability and Bioequivalence Evaluation

In Example 14, a comparative, randomized, single dose, 4-way Crossover Absolute Bioavailability (BA) and Bioequivalence (BE) study of Tranexamic Acid Tablet Formulations prepared in accordance with Examples 6 (modified release), 7 (immediate release), and 9 (delayed release) in Healthy Adult Women Volunteers under Fasting Conditions was performed. The design was a randomized, 4-way crossover, comparative BE and BA determination. All oral doses administered were 1.3 g. Twenty-eight (28) healthy non-smoking adult female volunteer subjects were enrolled in the study. Smokers, oral contraceptive users, those with a previous history of thromboembolic events and altered vision were excluded from the study. ECG monitoring was performed before, during and after the estimated times of peak serum tranexamic acid concentrations exposure. During the study, adverse events were captured and recorded throughout the trial period.

In the study, subjects were randomized to receive single oral 1.3 g (2×650 mg tablets) dose of tranexamic acid in tablet forms which included a modified release dosage form, an immediate release dosage form, and a delayed release dosage form. Subjects were also administered a single 1 g (10 ml) IV solution of tranexamic acid (100 mg/ml concentration).

The most frequently reported adverse events (Reported by greater than 10% of subjects) from the study of Example 14 are listed in the table below. The table lists the number of subjects reporting adverse events, and the percentage of subjects is in parentheses.

TABLE 9

Most Frequently Reported Adverse Events (Reported by >10% of Subjects) Number of Subjects Reporting Adverse Events

| Adverse Events | Treatment | | | | |
|---|---|---|---|---|---|
| | Delayed Release (2 × 650 mg) (n = 27) | Modified Release (2 × 650 mg) (n = 27) | Immediate Release (2 × 650 mg) (n = 27) | IV solution (10 × 100 mg/ml) (n = 27) | Total (n = 28) |
| Headache | 6 (22%) | 4 (15%) | 7 (26%) | 7 (26%) | 14 (50%) |
| Nausea | 0 (0%) | 0 (0%) | 2 (7%) | 10 (37%) | 12 (43%) |
| Dizziness | 1 (4%) | 0 (0%) | 0 (0%) | 11 (41%) | 12 (43%) |
| Feeling Hot | 0 (0%) | 0 (0%) | 0 (0%) | 6 (22%) | 6 (21%) |
| Nasal Congestion | 1 (4%) | 2 (7%) | 1 (4%) | 1 (4%) | 5 (18%) |
| Cough | 1 (4%) | 0 (0%) | 0 (0%) | 2 (7%) | 3 (11%) |
| Urine odor abnormal | 2 (7%) | 2 (7%) | 0 (0%) | 1 (4%) | 3 (11%) |

EXAMPLE 15

Dissolution tests of Modified Release and Immediate Release Formulations prepared in accordance with Examples 6 and 7 respectively were performed under USP 27 Dissolution Apparatus Type II Paddle Method @ 50 RPM in 900 ml water at 37±0.5° C. The delayed release formulation of Example 9 was dissolution tested under USP 27 Dissolution Apparatus Type II Paddle Method @ 50 RPM and 37±0.5° C. for 120 minutes in acid medium (1000 ml of 0.1N hydrochloric acid), subsequently followed by buffer medium (1000 ml of pH 6.8 phosphate buffer) for 45 minutes.

The results are listed in the tables below.

TABLE 10

Dissolution Results for the Immediate Release Formulation.

| | % | |
|---|---|---|
| Assay | 98.7% | |
| Content Uniformity | 99.0% | RSD 0.6% |
| Unknown Related Substance | NMT 0.2% Each | <0.1% |
| Total Related Substances and Impurities | NMT 2.0% Total | <0.1% |
| Dissolution Profile | | |
| 15 min. | 78.0% | |
| 30 min. | 99.0% | |
| 45 min. | 101.0% | |
| 60 min. | 102.0% | |

TABLE 11

Dissolution Results for the Modified Release Formulation

| | % | |
|---|---|---|
| Assay | 98.8% | |
| Content Uniformity | 100.6% | RSD 1.0% |
| Unknown Related Substance | NMT 0.2% Each | <0.1% |
| Total Related Substances and Impurities | NMT 2.0% Total | <0.1% |
| Dissolution Profile | | |
| 15 min. | 18.0% | |
| 30 min. | 41.0% | |
| 45 min. | 59.0% | |
| 60 min. | 76.0% | |
| 90 min. | 99.0% | |

TABLE 12

Dissolution Results for the Delayed Release Formulation.

| | % | |
|---|---|---|
| Assay | 100.0% | |
| Content Uniformity | 99.3% | RSD 0.60% |
| Unknown Related Substance | NMT 0.2% Each | <0.1% |
| Total Related Substances and Impurities | NMT 2.0% Total | <0.1% |
| Dissolution (Acid) 120 minutes followed by assay of medium (pH 1.0) | 3.0% | |
| Dissolution (Buffer) pH 6.8 Phos. Buffer 45 min. | 90.0% | |

Other variations or embodiments of the invention will also be apparent to one of ordinary skill in the art from the above descriptions and examples. Thus, the forgoing embodiments are not to be construed as limiting the scope of this invention.

What is claimed is:

1. A method of treating menorrhagia comprising administering by oral ingestion to a human patient in need of such treatment a therapeutically effective dose of a delayed release oral dosage form, wherein the delayed release oral dosage form comprises:

a core comprising tranexamic acid or a pharmaceutically acceptable salt thereof; and
a delayed release material coated on the core;
wherein the delayed release material comprises a copolymer of methacrylic acid with an acrylate or methacrylate ester;
wherein the delayed release oral dosage form provides for the delayed release of the tranexamic acid such that the dosage form is suitable for administration on a two or three times a day basis; and
wherein the delayed release oral dosage form provides an in-vitro dissolution release rate of the tranexamic acid or pharmaceutically acceptable salt thereof when measured by the USP 27 Dissolution Apparatus Type II Paddle Method @ 50 RPM and 37±0.5° C. wherein:
from 0% to about 10% by weight tranexamic acid or pharmaceutically acceptable salt thereof is released by about 120 minutes in acid medium (1000 ml of 0.1 N hydrochloric acid), and
at least 75% by weight of said tranexamic acid or pharmaceutically acceptable salt thereof is released by about 45 minutes after subsequent immersion of the oral dosage form in buffer medium (1000 ml of pH 6.8 phosphate buffer).

2. The method of claim 1, wherein the dosage form provides an in-vitro dissolution release rate of the tranexamic acid or pharmaceutically acceptable salt thereof when measured by the USP 27 Dissolution Apparatus Type II Paddle Method @ 50 RPM and 37±0.5° C. wherein:
from 0% to about 5% by weight tranexamic acid or pharmaceutically acceptable salt thereof is released by about 120 minutes in the acid medium (1000 ml of 0.1 N hydrochloric acid) and
at least 90% by weight tranexamic acid or pharmaceutically acceptable salt thereof is released by about 45 minutes after subsequent immersion of the oral dosage form in the buffer medium (1000 ml of pH 6.8 phosphate buffer).

3. The method of claim 2, wherein, after administration of said dosage form:
from 0% to about 5% by weight of said tranexamic acid is released from said dosage form after exposure of said dosage form for a period of 2 hours to an environmental fluid having a pH of less than 3, and
at least 95% by weight of said tranexamic acid is released from said dosage form after exposure of said dosage form for a period of 1 hour to an environmental fluid having a pH of at least 5.

4. The method of claim 1, wherein, after administration of said dosage form:
from 0% to about 10% by weight of said tranexamic acid is released from said dosage form after exposure of said dosage form for a period of 2 hours to an environmental fluid having a pH of less than 3, and
at least 75% by weight of said tranexamic acid is released from said dosage form after exposure of said dosage form for a period of 1 hour to an environmental fluid having a pH of at least 5.

5. The method of claim 1, wherein the tranexamic acid or pharmaceutically acceptable salt thereof is tranexamic acid.

6. The method of claim 1, wherein the delayed release material comprises a lower alkyl acrylic acid copolymer.

7. The method of claim 1, wherein the delayed release material comprises a copolymer of methacrylic acid with ethyl acrylate.

8. The method of claim 1, wherein the delayed release material comprises a copolymer of methacrylic acid with methyl methacrylate.

9. The method of claim 1, wherein the delayed release material comprises methacrylic acid copolymer, type C.

10. The method of claim 1, wherein the delayed release oral dosage form is in the form of a tablet.

11. The method of claim 1, wherein the delayed release oral dosage form is in the form of a capsule.

12. The method of claim 1, wherein the delayed release oral dosage form is in the form of a multiparticulate formulation.

13. The method of claim 1, wherein the delayed release oral dosage form comprises from about 585 to about 715 mg of tranexamic acid or pharmaceutically acceptable salt thereof.

14. The method of claim 13, wherein the delayed release oral dosage form comprises from about 617 to about 683 mg of tranexamic acid or pharmaceutically acceptable salt thereof.

15. The method of claim 14, wherein the delayed release oral dosage form comprises about 650 mg of tranexamic acid or pharmaceutically acceptable salt thereof.

16. The method of claim 13, wherein the method comprises administering three unit dosage forms of the delayed release dosage form on a twice a day basis for a total therapeutically effective daily dose of tranexamic acid ranging from about 3.51 gm to about 4.29 gm.

17. The method of claim 13, wherein the method comprises administering two unit dosage forms of the delayed release dosage form on a three times a day basis for a total therapeutically effective daily dose of tranexamic acid ranging from about 3.51 gm to about 4.29 gm.

18. The method of claim 17, wherein the method comprises administering a total daily dose of tranexamic acid of about 3.9 gm.

\* \* \* \* \*